United States Patent [19]
Volkin et al.

[11] Patent Number: 6,051,238
[45] Date of Patent: Apr. 18, 2000

[54] STABILIZERS FOR LYOPHILIZED MUMPS VACCINES

[75] Inventors: David B. Volkin, Doylestown; Carl J. Burke, Pennsburg; Su-Pi Sheu, Maple Glenn, all of Pa.

[73] Assignee: Merck & Co., Inc., Rahway, N.J.

[21] Appl. No.: 08/993,493

[22] Filed: Dec. 18, 1997

Related U.S. Application Data

[60] Provisional application No. 60/033,565, Dec. 20, 1996.

[51] Int. Cl.⁷ .................. A61K 39/12; A61K 39/165; C07H 3/04; C12N 7/04
[52] U.S. Cl. .................. 424/212.1; 424/199.1; 424/204.1; 424/189.1; 424/211.1; 424/217.1; 424/218.1; 424/229.1; 424/225.1; 424/278.1; 424/230.1; 424/219.1; 424/231.1; 435/235.1; 435/236
[58] Field of Search ............... 424/199.1, 204.1, 424/189.1, 211.1, 212.1, 217.1, 218.1, 229.1, 225.1, 278.1, 230.1, 219.1, 231.1; 435/235.1, 236

[56] References Cited

U.S. PATENT DOCUMENTS

| | | |
|---|---|---|
| 3,783,098 | 1/1974 | Kalnak et al. . |
| 3,915,794 | 10/1975 | Zygraich et al. . |
| 3,985,615 | 10/1976 | Kubo . |
| 4,000,256 | 12/1976 | Hilleman et al. . |
| 4,147,772 | 4/1979 | McAleer et al. . |
| 4,273,762 | 6/1981 | McAleer et al. . |
| 4,296,204 | 10/1981 | Grabner et al. ............... 435/235 |
| 4,337,242 | 6/1982 | Markus et al. . |
| 4,338,335 | 7/1982 | McAleer et al. . |
| 4,985,244 | 1/1991 | Makino et al. . |
| 5,024,836 | 6/1991 | McAleer et al. . |

FOREIGN PATENT DOCUMENTS

| | | |
|---|---|---|
| 028 563 | 5/1981 | European Pat. Off. . |
| 0130619 A2 | 1/1985 | European Pat. Off. . |
| 295 043 | 12/1988 | European Pat. Off. . |
| 568 726 | 11/1993 | European Pat. Off. . |
| 57007423 | 6/1980 | Japan . |

OTHER PUBLICATIONS

Bovarnick, et al., 1950, "The Influence of Certain Salts, Amino Acids, Sugars and Proteins on the Stability of Rickettsiae," J. Bacteriol. 59: 509–522.

McAleer, et al., 1980, "Stability on storage at varous temperatures of live measles, mumps and rubella vaccines in new stabilizer," J. Biological Stand. 8:281–287.

Howell, et al., Sep., 1983, "Effect of Sucrose Phosphate and Sorbitol on Infectivity of Enveloped Viruses During Storage," J. Clin. Microbiol. 18: 658–662.

Bennett, et al. (Karger, Basel, 1991), "The Effects of Freeze–Drying on the Potency and Stability of Live Varicella Virus Vaccine," Develop. Biological Stand., vol. 74, pp. 215–221.

*Primary Examiner*—Phuong T. Bui
*Attorney, Agent, or Firm*—Joseph A. Coppola; Jack L. Tribble

[57] ABSTRACT

Vaccine stabilizers, vaccine formulations and lyophilized vaccines with enhanced thermostability are disclosed. The vaccine formulations comprise an increased amount of a 6-carbon polyhydric alcohol (such as sorbitol), an increase amount of a disaccharide (such as sucrose) and an amount of a physiologically active buffer to adjust the pH from about 6.0 to about 7.0.

18 Claims, 14 Drawing Sheets

MEASLES VIRUS

FIG. 9

MUMPS VIRUS

FIG. 10

STABILIZERS FOR LYOPHILIZED MUMPS VACCINES

CROSS-REFERENCE TO RELATED APPLICATIONS

This application claims priority under 35 U.S.C. §119(e) from U.S. Provisional Patent Application Ser. No. 60/033,565, filed Dec. 20, 1996, the disclosures of which are incorporated herein by reference.

STATEMENT REGARDING FEDERALLY-SPONSORED R&D

Not applicable.

REFERENCE TO MICROFICHE APPENDIX

Not applicable.

FIELD OF THE INVENTION

The present invention relates to vaccine stabilizers, vaccine formulations and lyophilized vaccines which comprise increased amounts of a 6-carbon polyhydric alcohol, a disaccharide, and an amount of a physiologically active buffer to adjust the pH from about 6.0 to about 7.0.

BACKGROUND OF THE INVENTION

Measles is a negative-stranded RNA virus belonging to the genus Morbillivirus. The measles virus is highly contagious in its human host and is disseminated by coughing and sneezing from an infected host. The virus enters the bloodstream, spreads through the body and infects lymphoid tissues. A period of infectivity persists from approximately 6–7 days prior to appearance of a rash through about 2–3 days subsequent to appearance of the rash. Prodromal symptoms of fever and malaise occur about 10 days subsequent to exposure. This is followed by a hacking cough, coryza, conjunctivitis, and possibly photophobia. Koplik spots appear approximately 2 days prior to appearance of the rash. The stage of maximal severity of the infection the patient may complain of headaches, abdominal pain, vomiting, diarrhea, and/or myalgia.

Mumps is a negative-stranded RNA virus belonging to the genus Paramyxovirus. The incubation period for the mumps virus is usually 17–21 days, but may range from 8 to 37 days. After infection and growth in the respiratory tract, the virus enters the bloodstream where it is systemically delivered to various body tissues. Mumps is characterized by sweling and tenderness of the parotid gland and occasionally through other salivary glands. Prior to swelling the patient may experience pain behind the jaw and just below the ear, which is increased by pressure and movement of the jaws. More severe cases may include prodromal symptoms such as anorexia, headache, vomiting, myaglia and high fever.

Rubella virus is a positive-stranded RNA virus and sole member of family Togaviridae which causes german measles. Rubella infection usually occurs by airborne spread of infected droplets. Many rubella infections are sub clinical, with a ratio of approximately 2:1 of inapparent to overt disease. The incubation period for rubella virus is 14–21 days, with a characteristic pattern of adenopathy, rash and low grade fever. Rubella during early pregnancy frequently results in fetal infection, which may be chronic and may produce a spectrum of illness known as Congenital Rubella Syndrome (CRS).

Chickenpox (varicella-zoster) virus is a herpes virus, which are a group of intranuclear, double-stranded DNA viruses that can establish a latent infection many years after a primary infection. Chickenpox is one of the most common and highly communicable diseases and occurs primarily in childhood. A rash is observed generally over the entire body together with an attack of fever which occurs after an incubation period running between 14 and 17 days. The disease results in a muscular rash which may, in many cases, form pustules and, in extreme cases, leave scars. Other complications such as central nervous system disturbance, myelitis and neuritis were known to occur as results from chickenpox. A live attenuated vaccine and a process for making the vaccine is known for chickenpox and is disclosed in U.S. Pat. No. 3,985,615, issued to Kubo.

For the past several decades a routine vaccination schedule for infants and children has included immunization with a live attenuated trivalent vaccine for measles, mumps and rubella at approximately 15 months of age and again sometime between ages 4 through 6 or at middle school age. Also available to the public are various monovalent (e.g., measles, mumps, rubella or chicken pox), divalent (e.g., measles-mumps) and tetravalent (e.g., measles-mumps-rubella-chicken pox) vaccines.

Vaccine stabilizers are well known in the art as chemical compounds added to a vaccine formulation to enhance vaccine stability during low temperature storage or storage post-lyophilization.

One such chemical stabilizer is referred to as SPGA and is described in Bovamick et al., 1950, *J. Bact.* 59:509–522. One liter of SPGA was disclosed to contain 0.218M sucrose (74.62 g), 0.00376 M $KH_2PO_4$ (0.52 g), $K_2HPO_4$ 0.0071 M (1.25 g), potassium glutamate 0.0049 M (0.912 g) and 1% serum albumin (10 g).

U.S. Pat. No. 3,783,098, issued to Calnek, et al., discloses a modification of SPGA wherein monosodium glutamate is substituted for monopotassium glutamate. Also, use of a starch hydrosylate such as glucose or dextran maybe substituted wholly or partly for sucrose. Finally, casein or PVP may be substituted wholly or partly for albumin as described (see also U.S. Pat. No. 3,915,794, issued to Zygrsich, et al.).

U.S. Pat. No. 4,000,256, issued to Hilleman, et al., describes an SPGA stabilizer containing per liter of sterile distilled water: 74.62 g sucrose, 0.45 g $KH_2PO_4$, 1.35 g $K_2HPO_4$, 0.956 g monosodium L-glutamate, and 40 ml of a 25% solution of human albumin.

In general, an SPGA stabilizer contains from about 2 to about 10% of a particular sugar, (e.g., sucrose), from about 0.05 to about 0.3% of a mono- or dibasic alkali metal phosphate salt or mixture thereof, e.g., $KH_2PO_4$, $K_2HPO_4$, $NaH_2PO_4$ or $Na_2HPO_4$, from about 0.05 to about 0.2% of a glutamic acid alkali metal salt, e.g., sodium or potassium glutamate; and from about 0.5% to about 2% serum albumin, e.g., bovine serum albumin or human albumin.

Another chemical stabilizer known in the art comprises hydrolyzed gelatin, Medium O and sorbitol. This chemical stabilizer, disclosed in U.S. Pat. No. 4,147,772, issued to McAleer, et al., comprises approximately 3.5% hydrolyzed gelatin, 3.5% sorbitol, 1.0% Medium 199, along with minimal amounts of sodium bicarbonate and phenol red.

A vaccine stabilizer modified from U.S. Pat. No. 4,147,772 is disclosed in U.S. Pat. No. 4,273,762, issued to McAleer, et al. This stabilizer comprises the components disclosed in U.S. Pat. No. 4,147,772 as well as minute amounts of DPG solution, which contains, among other compounds, cysteine, glutathionine, ascorbic acid, vitamin A and USP.

Despite theses advances in the area of vaccine formulations, there remains a distinct need for live vaccine formulations with improved thermostability and shelf-life, especially live measles, mumps and rubella vaccines. None of the prior art stabilizers impart the desired enhanced sustained level of stability. The present invention addresses and meets the long felt need for a stabilizer and live vaccine formulation with increased thermostability subsequent to lyophilization.

SUMMARY OF THE INVENTION

The present invention relates to vaccine stabilizers, vaccine formulations, and live attenuated lyophilized vaccines which impart increased thermostability.

The vaccine formulation of the present invention comprises viral and stabilizer components which result on a gram per liter basis from about 15 to about 90 grams per liter of a 6-carbon polyhydric alcohol, including but not limited to sorbitol, mannitol and dulcitol; from about 10 to about 70 grams per liter of a disaccharide, including but not limited to sucrose, lactose, maltose or trehalose and an amount of a physiologically active buffer to adjust the pH from about 6.0 to about 7.0. It is preferred in the present invention that the 6-carbon polyhydcic alcohol be sorbitol and the disaccharide be sucrose.

In another embodiment of the present invention, the vaccine formulation contains sorbitol as the 6-carbon polyhydric alcohol, from about 15 to about 90 grams per liter; the disaccharide sucrose, from about 10 to about 70 grams per liter; and, the pH of the vaccine formulation is controlled through citrate-phosphate combinations to ensure buffering across a pH range of about 6.0 to about 7.0 by one of two approaches: addition of phosphate at a concentration from about 7.5 mM to about 75 mM or addition of a phosphate-:citrate combination with a phosphate concentration from about 7.5 mM to about 75 mM and a citrate concentration from about 30 mM to about 0.4M.

In an additional embodiment of the present invention, the vaccine formulation contains sorbitol as the 6-carbon polyhydric alcohol, from about 15 to about 90 grams per liter; the disaccharide sucrose, from about 10 to about 70 grams per liter; and, the pH of the vaccine formulation is controlled through addition of a phosphate buffer to ensure buffering across the preferred pH range of about 6.0 to about 7.0

The vaccine formulations of the present invention preferably include one or more additional components, alone or in a biologically effective combination, which provides a vaccine with enhanced thermostability characteristics; including but not limited to hydrolyzed gelatin from about 10 to 50 grams per liter, sodium chloride from about 1 to about 6 grams per liter; sodium bicarbonate in amounts to about 1.5 g/l, preferable from about 0.2 g/l to about 1.2 g/l; human serum albumin at about 0.5 to 1.0 gram per liter, or approximately 0.3 to about 1.0% by dry weight of the lyophilized form of the vaccine; and cell culture medium which is a nutrient medium which promotes cell growth in vitro, including but not limited to known cell culture media such as Solution 199, Medium T, Medium O, Dubecco's Modified Eagles Medium, Mjninl Essential Medium, and Basal Medium Eagle. Preferred media components include biologically effective amounts of Medium O, Medium T and Solution 199. Other components of the vaccine formulation of the present invention may include, but are not limited to, biologically active amounts of an antibiotic (e.g., neomycin) and a pH indicator (e.g., phenol red).

Therefore, vaccine formulations of the present invention may comprise sorbitol as the 6-carbon polyhydric alcohol, from about 15 to about 90 grams per liter; the disaccharide sucrose, from about 10 to about 70 grams per liter; a biologically effective concentration of a cell culture medium (preferably Medium O), a biologically effective concentration of a salt (preferably NaCl), a biologically effective concentration of a bicarbonate (preferably $NaHCO_3$), a citrate-phosphate combination to ensure buffering across the preferred pH range as well as several additional components, including but not limited to neomycin and phenol red. The addition of bicarbonate in varying amounts may alter the formulation pH within a biologically acceptable range.

The vaccine formulations of the present invention may also comprise sorbitol as the 6-carbon polyhydric alcohol, from about 15 to about 90 grams per liter; the disaccharide sucrose, from about 10 to about 70 grams per liter; a biologically effective concentration of a cell culture medium (preferably Medium O), a biologically effective concentration of a salt (preferably NaCl), a biologically effective concentration of a bicarbonate (preferably $NaHCO_3$), a phosphate buffer to ensure the preferred pH range as well as several additional components, including but not limited to neomycin and phenol red. Again, the addition of bicarbonate in varying amounts may alter the formulation pH within a biologically acceptable range.

An integral aspect of a preferred portion of the vaccine formulations of the present invention is the dual presence of sucrose and sorbitol. The range of sorbitol is from about 15 to about 90 grams per liter while sucrose is present in the range from about 10 to about 70 grams per liter. A preferred range of sorbitol in the vaccine formulations of the present invention is from about 35 to about 75 grams per liter. An especially preferred range of sorbitol in the vaccine formulation of the present invention is from about 45 grams per liter to about 60 grams per liter. A preferred range of sucrose in the vaccine formulations of the present invention is from about 15 to about 55 grams per liter. An especially preferred range of sucrose in the vaccine formulation of the present invention is from about 20 grams per liter to about 45 grams per liter.

Especially preferred formulation are shown in Table 1 as Formulations 1–12. These formulations direct the artisan of ordinary skill to generate additional vaccine formulations based on the dual presence of sucrose and sorbitol within the disclosed ranges. Therefore, the preferred component ranges disclosed in this specification allow for generation of vaccine formulations which, among other characteristics, exhibit improved thermostability over vaccine formulations known in the art.

BRIEF DESCRIPTION OF THE DRAWINGS

Figures 9, 10:
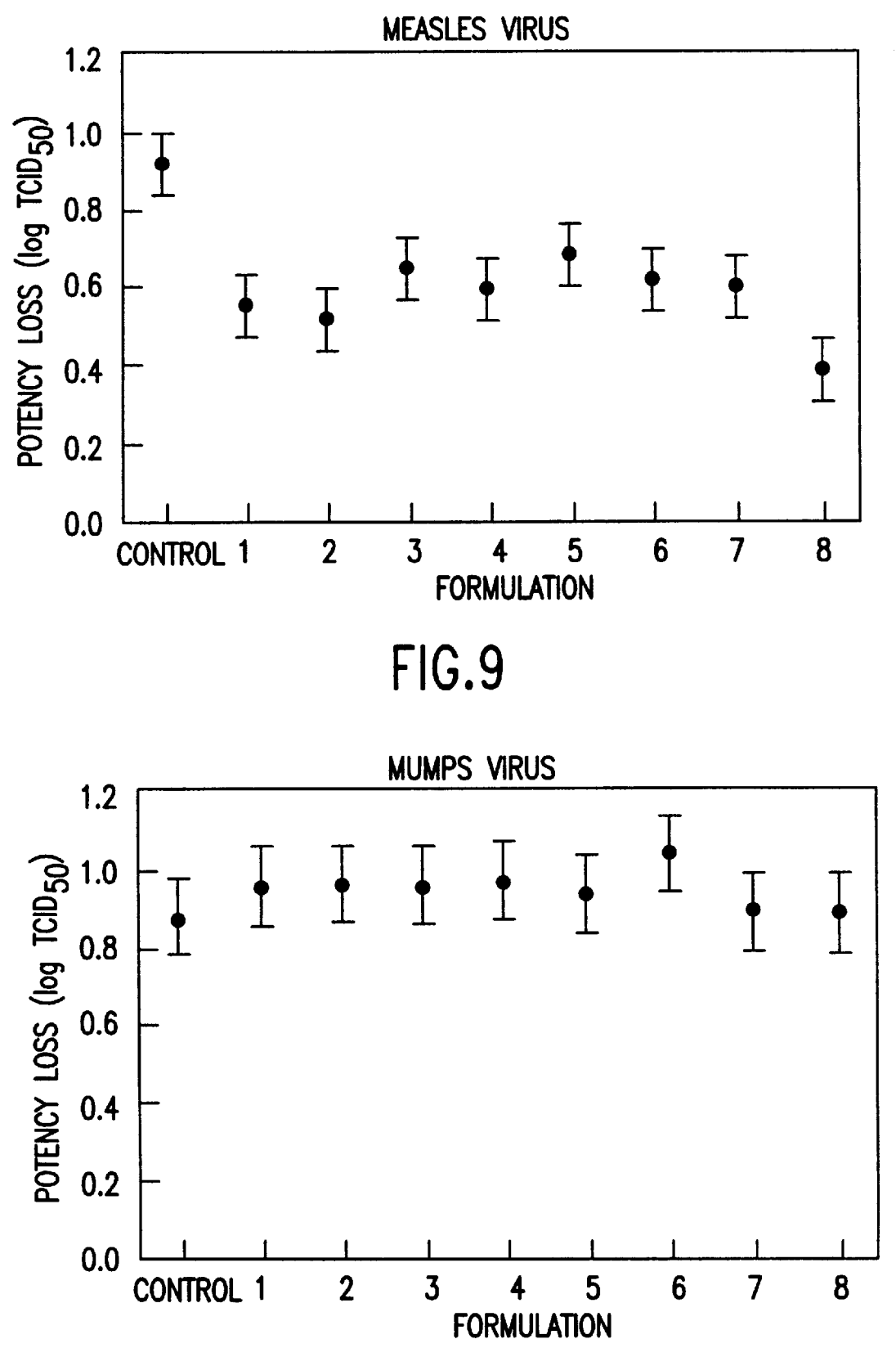

FIG. 9 shows the thermostability of measles virus for the control stabilizer and Formulation 1- Formulation 8 of Table 1 after post-lyophilization storage for 1 week at 37° C. Increased thermostability is shown as a decrease in potency loss, measured as the log $TCID_{50}$. Bars represent the standard error of the mean.

FIG. 10 shows the thermostability of mumps virus for the control stabilizer and Formulation 1- Formulation 8 of Table 1 after post-lyophilization storage for 1 week at 37° C. Increased thermostability is shown as a decrease in potency loss, measured as the log $TCID_{50}$. Bars represent the standard error of the mean.

DETAILED DESCRIPTION OF THE INVENTION

Figure 1:
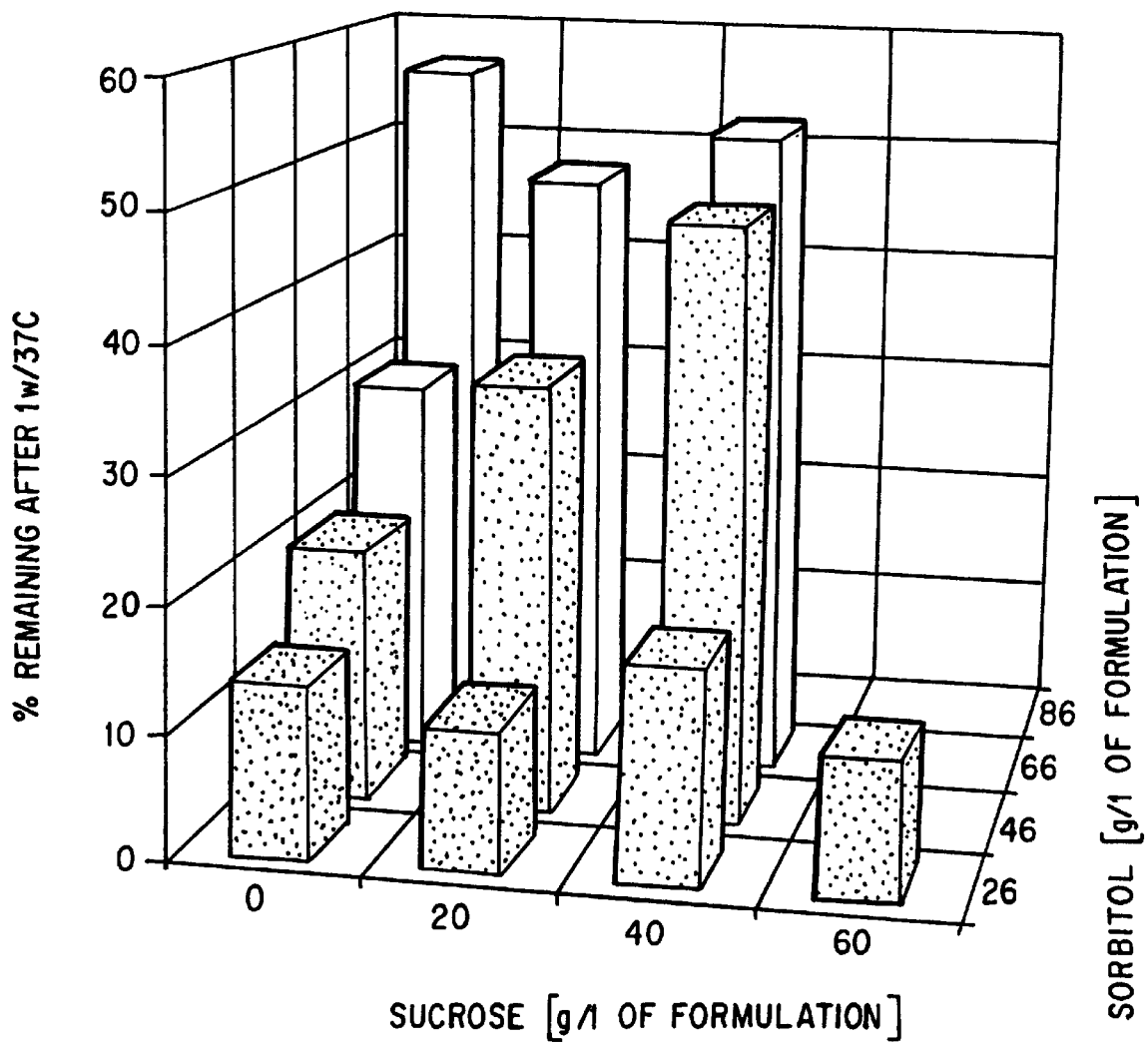
FIG. 1 shows the effect of various sorbitol and sucrose concentrations on the thermostability of a live lyophilized measles vaccine.

The present invention relates to vaccine stabilizers, vaccine formulations, and live attenuated lyophilized vaccines which impart increased thermostability. The initial vaccine of the present invention comprises viral and stabilizer components which result on a gram per liter of final vaccine, prior to lyophilization, from about 15 to about 90 grams per liter of a 6-carbon polyhydric alcohol, including but not limited to sorbitol, mannitol and dulcitol; from about 10 to about 70 grams per liter of a disaccharide, including but not limited to sucrose, lactose, maltose or trehalose and an amount of a physiologically active buffer to adjust the pH from about 6.0 to about 7.0.

In a particular embodiment of the present invention the vaccine formulation contains sorbitol as the 6-carbon polyhydric alcohol, from about 15 to about 90 grams per liter.

In another particular embodiment of the present invention the vaccine formulation contains the disaccharide sucrose, from about 10 to about 70 grams per liter.

In a preferred embodiment of the present invention the vaccine formulation contains sorbitol as the 6-carbon polyhydric alcohol, from about 15 to about 90 grams per liter and the disaccharide sucrose, from about 10 to about 70 grams per liter.

In another aspect of the invention, the vaccine formulation contains sorbitol as the 6-carbon polyhydric alcohol, from about 15 to about 90 grams per liter; the disaccharide sucrose, from about 10 to about 70 grams per liter; and the pH of the vaccine formulation is controlled through citrate-phosphate combinations to ensure buffering across a pH range of about 6.0 to about 7.0 by one of two approaches: addition of phosphate at a concentration from about 7.5 mM to about 75 mM or addition of a phosphate:citrate combination with a phosphate concentration from about 7.5 mM to about 75 mM and a citrate concentration from about 30 mM to about 0.4M.

In another aspect of the invention, the vaccine formulation contains sorbitol as the 6-carbon polyhydric alcohol, from about 15 to about 90 grams per liter; the disaccharide sucrose, from about 10 to about 70 grams per liter; and the pH of the vaccine formulation is controlled through addition of a phosphate buffer to ensure buffering across the preferred pH range of about 6.0 to about 7.0.

The vaccine formulation of the present invention may preferably include one or more additional components, alone or in a biologically effective combination, which provides a vaccine with enhanced thermostability characteristics; including but not limited to hydrolyzed gelatin to about 10 to 50 grams per liter; sodium chloride to about 10 g/l and preferably from about 1 to about 6 grams per liter; sodium bicarbonate in amounts to about 1.5 g/l, preferably from about 0.2 g/l to about 1.2 g/l; human serum albumin to about 1.5 g/l and preferably at about 0.5 to 1.0 g/l, or approximately 0.3 to about 1.0% by dry weight of the lyophilized form of the vaccine; and cell culture medium which is a nutrient medium which promotes cell growth in vitro, including but not limited to known cell culture media such as Solution 199, Medium T, Medium O, Dubecco's Modified Eagles Medium, Minimal Essential Medium, and Basal Medium Eagle. Preferred media components include biologically effective amounts of Medium O, Medium T and Solution 199. Other components of the vaccine formulation of the present invention may include, but are not limited to, biologically active amounts of an antibiotic (e.g., neomycin) and a pH indicator (e.g., phenol red).

Medium O comprises 68.2 ml/l of 10×Solution 199,680 ul/l of Solution DPG (Solution DPG is, per liter, 50 mg ascorbic acid, 100 mg L-cysteine, 50 mg glutathione followed by the addition of 900 ml double distilled $H_2O$, 10 ml of 95% ethyl alcohol, 5 ml polysorbate 80 NF, 25 mg vitamin A [crystalline alcohol], followed by 85 ml of double distilled $H_2O$ and 10 g of adenosine triphosphate), 30.7 ml of 2.8% sodium bicarbonate solution and 340 ul of a 2.0% phenol red solution.

Medium T is, per liter, 10 ml of 25% human serum albumin, 112 mg potassium phosphate (monobasic), 338 mg potassium phosphate (dibasic), 239 mg monosodium L-glutamate monohydrate, 18.6 g sucrose, followed by the addition of 842 ml of double distilled $H_2O$, 75 ml of 10×Solution 199, 750 ul/l of Solution DPG, 60 ml of 2.8% sodium bicarbonate solution and 420 ul of a 2.0% phenol red solution.

Therefore, vaccine formulations of the present invention may also comprise sorbitol as the 6-carbon polyhydric alcohol, from about 15 to about 90 grams per liter; the disaccharide sucrose, from about 10 to about 70 grams per liter; a biologically effective concentration of a cell culture medium (preferably Medium O), a biologically effective concentration of a salt (preferably NaCl), a biologically effective concentration of a bicarbonate (preferably $NaHCO_3$) and either a citrate-phosphate combination or phosphate alone to ensure buffering across the preferred pH range of 6.0 to 7.0. The addition of bicarbonate in varying amounts may alter the formulation pH within a biologically acceptable range when added in combination with a phosphate-citrate buffer or phosphate buffer alone.

The vaccine formulation of the present invention contains from about 15 to about 50 grams per liter of hydrolyzed gelatin. Partially hydrolyzed gelatin has, as its name infers, been subjected to partial hydrolysis to yield a partially hydrolyzed gelatin having an average molecular weight of about 3,000 Da. This gelatin hydrolysis product has approximately the same amino acid composition as gelatin. Unlike gelatin which forms gels but is insoluble in cold water, hydrolyzed gelatin does not gel but is soluble in cold water and other common liquids such as milk and orange juice. Aqueous solutions containing up to about 10% hydrolyzed gelatin do not increase appreciably in viscosity. Above about 10% concentration, viscosity increases slowly. At about 50% concentration, solutions are quite viscous. The typical amino acid composition of hydrolyzed gelatin is known. Partially hydrolyzed gelatin may be obtained from any number of commercial sources, for instance under the tradename Dynagel. Partially hydrolyzed gelatin may also be obtained by enzymatic hydrolysis of gelatin by means of a proteolytic enzyme, such as, for example, papain, chymopapain, and bromelin, although other known hydrolysis means may be employed, e.g., acid hydrolysis. A preferred range of hydrolyzed gelatin in the disclosed vaccine formulations of the present invention is from about 20 grams per liter to about 35 grams per liter. An especially preferred range of hydrolyzed gelatin in the disclosed vaccine formulations of the present invention is from about 25 grams per liter to about 30 grams per liter.

An integral aspect of a preferred portion of the vaccine formulations of the present invention is the dual presence of sucrose and sorbitol. The range of sorbitol is from about 15 to about 90 grams per liter while sucrose is present in the range from about 10 to about 70 grams per liter. A preferred range of sorbitol in the vaccine formulations of the present invention is from about 35 to about 75 grams per liter. An especially preferred range of sorbitol in the vaccine formulation of the present invention is from about 45 grams per liter to about 60 grams per liter. A preferred range of sucrose in the vaccine formulations of the present invention is from about 15 to about 55 grams per liter. An especially preferred range of sucrose in the vaccine formulation of the present invention is from about 20 grams per liter to about 45 grams per liter.

The combination of a 6-carbon polyhydric alcohol and a disaccharide (sorbitol plus sucrose) and the total concentration of both components in the vaccine stabilizer and formulation of the present invention results in a dramatic improvement in measles virus stability not seen in currently available stabilizers, modest improvements in mumps virus stability and no significant change in rubella virus stability subsequent to lyophilization. A pH of 6.2 is disclosed as advantageous for measles virus stability while not dramatically affecting mumps stability from a known stabilizer pH of 6.5. Changes in the osmotic and ionic strength as compared to a control stabilizer from 440–600 mOsm does not appear to affect the thermal stability of the M-M-R®II vaccine. The removal of tissue culture components from various stabilizers of the present invention imparts better drying characteristics during lyophilization while decreasing overall osmolality in the high sugar content vaccine formulations of the present invention.

Therefore, the essence of the invention centers around a substantial total increase in the concentration of sugars in the vaccine formulation prior to lyophilization. As disclosed in this section as well as the foregoing examples, a 6-carbon polyhydric alcohol (e.g., sorbitol) and a disaccharide (e.g., sucrose) are added in substantially increasing amounts to generate a vaccine stabilizer for combination with bulk viral preparations to generate vaccine formulations for lyophilization which result in the before-mentioned increase in thermostability.

The preferred component ranges disclosed in this specification allow for generation of vaccine formulations which, among other characteristics, exhibit improved thermostability over vaccine formulations known in the art. Formulations 1–12 as exemplified is this specification will direct the artisan of ordinary skill to generate additional vaccine formulations based on the dual presence of sucrose and sorbitol within the disclosed ranges. Formulations 1–12 may comprise or may omit additional components such as neomycin and phenol red. In other words, variations in ratios, concentrations and presence of additional components for each formulation is contemplated.

The present invention is also exemplified by testing stability of a live attenuated measles-mumps-rubella virus vaccine. However, the present invention includes, but in by no means limited to, monovalent vaccines (e.g., mumps, measles, rubella, chicken pox), divalent vaccines (e.g., measles-mumps), trivalent vaccines (e.g., measles-mumps-rubella) and tetravalent vaccines (e.g., measles-mumps-rubella-chicken pox). Therefore, examples of viruses which may comprise a vaccine of the present invention include but are not necessarily limited to measles, mumps, rubella, varicella zoster, polio or hepatitis, herpes simplex 1, herpes simplex 2, or combinations thereof, such as various divalent, trivalent or etravalent vaccines.

The ranges of various stabilizer and final vaccine formulations are presented on a gram per liter basis of the final vaccine preparation. One of ordinary skill in the art will be well aware that differing volumes of stabilizer to vaccine may be utilized to practice the claimed invention, which in turn will require changes to the concentration of stabilizer components. Such changes are contemplated in this disclosure by providing the effective concentration of the various chemical components on the basis of g/l of final live vaccine prior to lyophilization. The invention is exemplified, but by no means limited to, utilization of 3:1 stabilizer:virus combination to generate the final vaccine for lyophilization. However, the artisan may choose different ratios or use bulk viral preparations with altered concentration of major chemical components. Therefore, this artisan will prepare a stabilizer with the appropriate concentration of these components (e.g., sucrose, sorbitol, hydrolyzed gelatin, etc.), taking into account (1) the presence of these major components, if at all, in the virus preparation; and, (2) the planned ratio of stabilizer to virus preparation to be used in preparing the final vaccine.

For example, a preferred vaccine of the present invention is a measles-mumps-rubella trivalent vaccine. Such a preferred measles-mumps-rubella trivalent vaccine of the present invention will comprise at least the major components of Formulations 1–12 of Table 1. Alternatively, major components such a hydrolyzed gelatin, sucrose, sorbitol, phosphate or a phosphate:citrate combination may be added to a vaccine formulation in the respective ranges disclosed throughout this specification. The measles-mumps-rubella viruses will commonly be mixed in a 3:1 stabilizer/buffer:virus combination. In these exemplified trivalent formulations, approximately 2.1 g/l of hydrolyzed gelatin, 2.1 g/l of sorbitol, 3.7 g/l of sucrose, and 1.54 g/l of NaCl are present in the viral media. Additionally, the stabilizer may be added at 67.5% of the final volume of the vaccine formulation with the addition of a phosphate buffer or phosphate:citrate combination comprising 7.5% of the final volume of the vaccine formulation. Therefore, components of preferred stabilizer solutions for use in such a stabilizer/buffer virus combination are easily determined on the basis of the initial contribution of components from both the viral containing media and buffer.

Table 2 shows the major components of a stabilizer associated with Formulations 1–12 of the present invention when prepared at a 3:1 stabilizer/buffer:virus ratio. The concentration ranges for the major components of the stabilizer and final vaccine formulation are approximately the same. Therefore, a vaccine stabilizer of the present invention will also comprise at least, on a gram per liter basis, from about 15 to about 90 grams per liter of a 6-carbon polyhydric alcohol, including but not limited to sorbitol, mannitol and dulcitol; from about 10 to about 70 grams per liter of a disaccharide, including but not limited to sucrose, lactose, maltose or trehalose. A particular stabilizer of the present invention will also contain sorbitol as the 6-carbon polyhydric alcohol, from about 15 to about 90 grams per liter and sucrose, from about 10 to about 70 grams per liter. This particular stabilizer will also comprise from about 15 to about 50 grams per liter of hydrolyzed gelatin, preferably from about 20 to 30 grams per liter and especially from about 25 to about 30 grams per liter. As with the disclosed final vaccine formulations of the present invention, the preferred stabilizers of the present invention comprise sorbitol from about 35 to about 75 grams per liter, with an especially preferred range from about 40 grams per liter to about 60 grams per liter. Also, a preferred range of sucrose in the stabilizers of the present invention is from about 15 to about 55 grams per liter, with an especially preferred range of sucrose ranging from about 15 grams per liter to about 45 grams per liter.

The following examples are provided for the purpose of illustrating the present invention without, however, limiting the same thereto.

EXAMPLE 1

The control stabilizer used in Examples 1–3 is a known stabilizer disclosed in U.S. Pat. No. 4,273,762, issued to McAleer, et al. This stabilizer comprises the stabilizer components disclosed in U.S. Pat. No. 4,147,772, as well as minute amounts of DPG solution (50 mg ascorbic acid, 100 mg L-cysteine, 50 mg glutathione followed by the addition of 900 ml double distilled $H_2O$, 10 ml of 95% ethyl alcohol, 5 ml polysorbate 80 NF, 25 mg vitamin A [crystalline alcohol], followed by 85 ml of double distilled $H_2O$ and 10 g of adenosine triphosphate). U.S. Pat. No. 4,273,762 and U.S. Pat. No. 4,147,772 are hereby incorporated by reference. A trivalent vaccine comprising measles virus (More Attenuated Enders Edmonston strain; minimum dose=3.0 $TCID_{50}$, target fill=3.8 $TCID_{50}$) mumps virus (Jeryl Lynn 'strain; minimum release=4.3 $TCID_{50}$/dose; target fill=5.0 $TCID_{50}$/dose) and rubella virus (Wistar RA 27/3 strain; minimum release=3.0 $TCID_{50}$/dose; target fill=3.8 $TCID_{50}$/dose) is utilized in Examples 1–3 as a control vaccine. This lyophilized trivalent vaccine is sold under the tradename M-M-R®II. The control M-M-R®II formulation comprises, by grams per liter final vaccine of. 28.9 g hydrolyzed gelatin, 28.9 g sorbitol, 10.59 g phosphate, 4.9 g NaCl, 3.74 g sucrose, 0.9 g sodium bicarbonate, 0.66 g glucose, and 0.62 g human serum albumin. The composition of the control vaccine formulation, on a percent basis of volume prior to lyophilization, 67.5% control stabilizer, 7.5% 1M phosphate, 20% of a measles virus bulk/mumps virus bulk/Medium T composition (Medium T comprising, on a g/l basis, 0.45 g phosphate, 6 g NaCl, 18.7 g sucrose, 1.68 g sodium bicarbonate, 0.75 g glucose, 2.5 g human serum albumin and 8.4 mg phenol red) and 5% of a rubella virus bulklrubella diluent (e.g., such a rubella diluent may include but by no means be limited to, on a per liter basis, 9.6 ml of 25% human serum albumin, 42.9 g hydrolyzed gelatin, 5.6 g of Eagles MEM, 42.9 g sorbitol, 6.8 NaCl, 1 g glucose, 2.4 g human serum albumin and 12 mg phenol red (600 ul of a 2.0% phenol red solution).

Methods—Various stabilizer:MMR vaccine formulations were tested at laboratory and production scale with up to three different lots of bulk virus. Lyophilized measles virus losses approximately 1.0 log, or 90%, of infectious titer after one week at 37° C. in the control stabilizer. The stabilizer:virus formulations of the present invention must improve the thermostability characteristics of a lyophilized measles vaccine while not unacceptably compromising the stability of mumps or rubella viruses. Based on the performance of the potency assay ($TCID_{50}$), the thermal stability of measles virus observed in these experiments should be no less than a 0.7 log loss (>22% remaining) after one week at 37° C. Potencies for all three viruses for the hydrolyzed gelatin and buffer concentration experiments were determined. A $TCID_{50}$ assay was performed in a 1×6 format (i.e., one vial in 6 unique setups, typically different days). All other experimental conditions (pH, sugar concentration, ionic strength, medium O replacement) were tested using plaque assays in a 1×6 format.

Samples of M-M-R®II were assayed for thermal stability by incubation at 30° C. and 37° C. for-one week and compared to control vials stored at −70° C. Samples that are incubated at 30° C. typically display similar stability trends as those incubated at 37° C. but show larger differences between formulations. Liquid samples were also collected and frozen without being lyophilized then assayed to determine yield across lyophilization. A total of 3960 vials were assayed.

Moisture content of lyophilized vaccine was measured using an Aquatest IV (Karl Fisher method) and represent the average of 4 replicate vials.

Samples of M-M-R®II were lyophilized in a Usifroid cabinet. An initial shelf temperature ramp to −15° C. was performed during primary drying to rapidly raise the product temperature before the shelf temperature was decreased to −25° C. for the remainder of primary drying. In this manner, the product temperature is kept near −40° C. during all of prima drying, the putative Tg' of the control stabilized vaccine over which physical collapse of the lyophilized cake may occur. In addition, two-slot stoppers (West 4405) were used for all studies and were predried in a vacuum oven at 140° C. for at least 6 hours and used within 24 hours. Prior to loading into the lyophilizer, all formulations were frozen on the lyophilizer shelf which was precooled to −45° C. For high sugar formulations, the final shelf temperature and hold time was extended to ensure lower moisture content.

Figure 2:
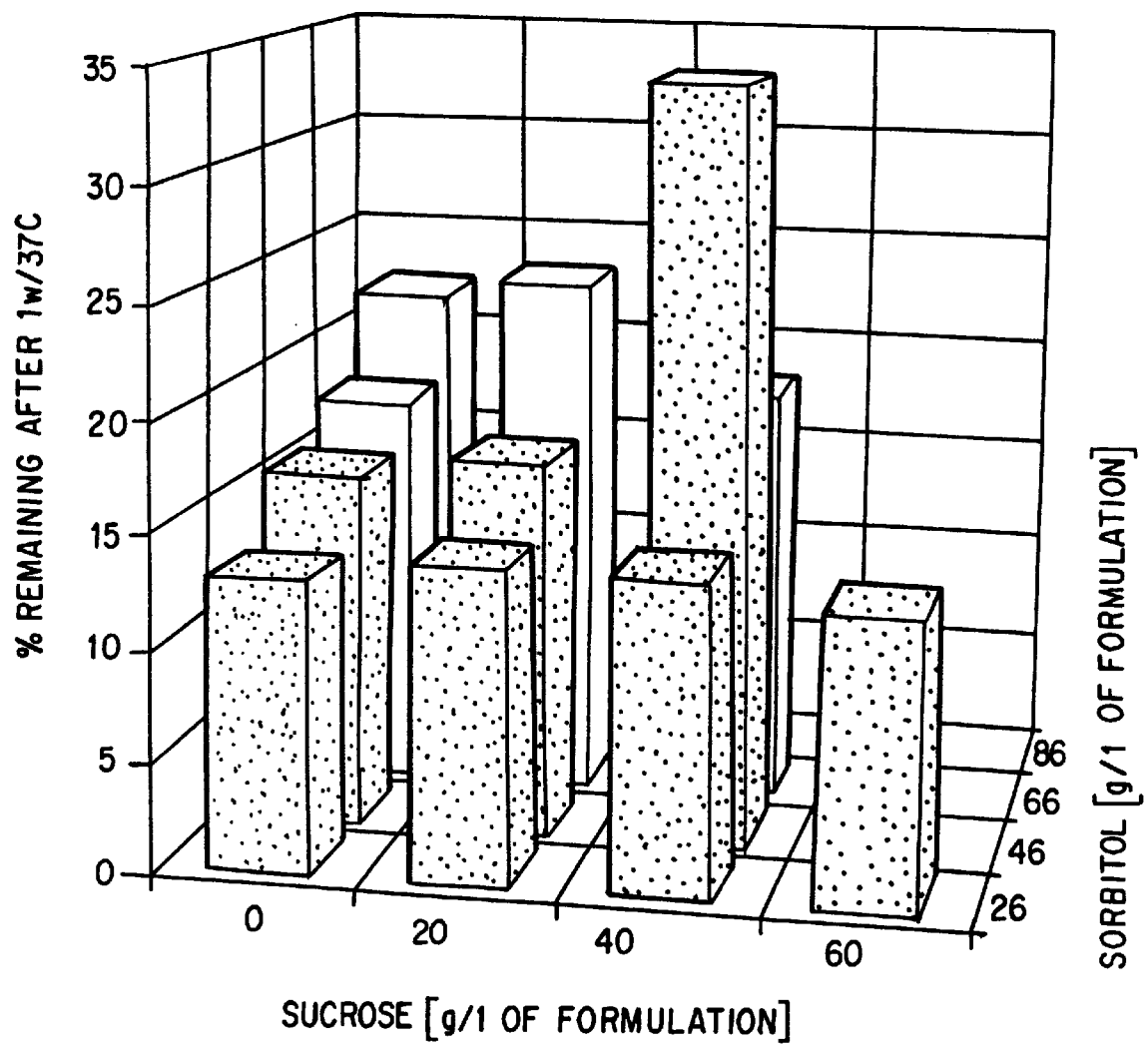
FIG. 2 shows the effect of various sorbitol and sucrose concentrations on the thermostability of a live lyophilized mumps vaccine.

Effect of Sugar Concentration—This example shows that substantial increase in sucrose and sorbitol concentrations in the vaccine formulation results in increased thermal stability for measles and mumps viruses. To determine the optimal concentrations and combinations of sorbitol and sucrose, various combinations were evaluated. The formulation for M-M-R®II contains 2.7% sorbitol. The addition of sucrose alone does not affect the thermal stability of MeV up to concentrations of 6% final sucrose. Added sorbitol does, however, have a marked effect on the thermal stability of MeV which is directly related to the final concentration of sorbitol. Surprisingly, sucrose added to formulations containing additional sorbitol also results in a dramatic stabilizing effect. FIG. 1 shows that at increased concentrations of sorbitol, sucrose or sorbitol and sucrose results in comparable increases in measles virus (MeV) thermal stability. The stability of mumps vrrus (MuV) displays similar trends although the changes are generally smaller (FIG. 2). The stability of rubella virus (RuV) is not significantly affected by a change in sugar concentrations.

Figure 3:
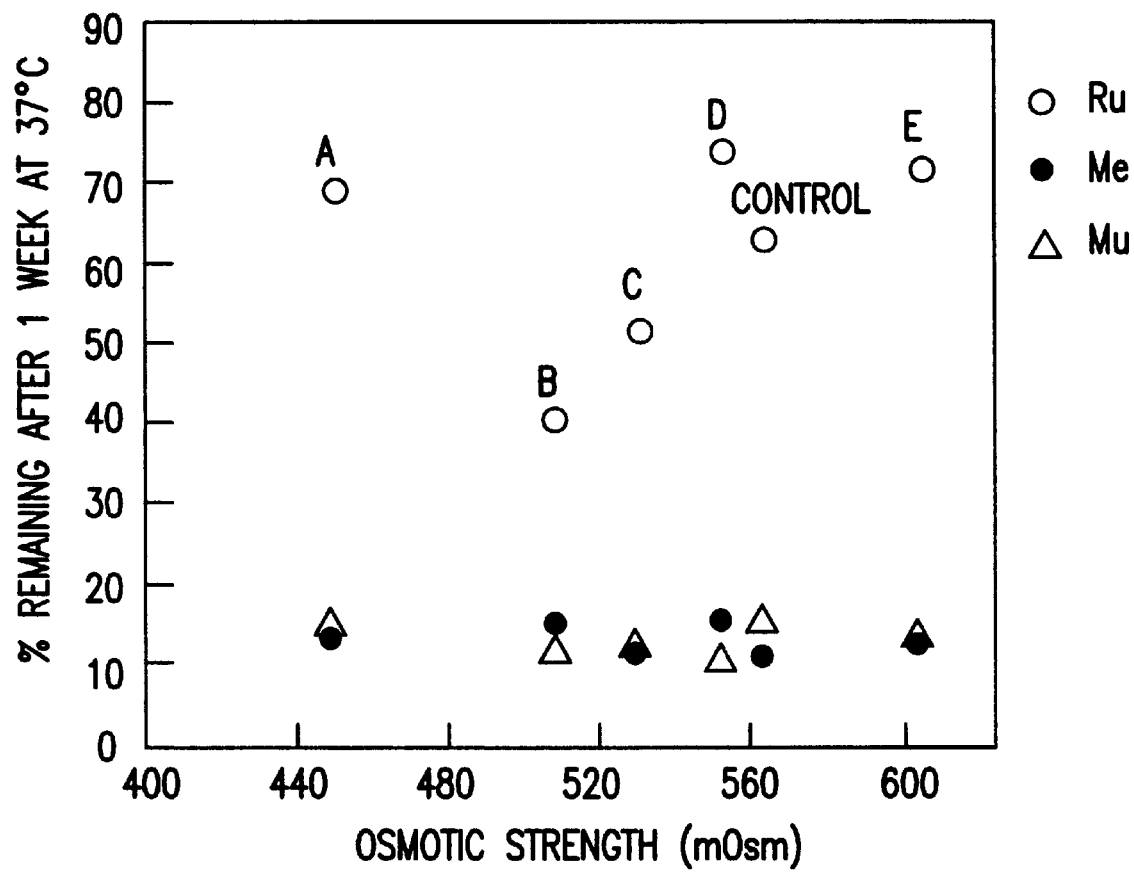
FIG. 3 shows the effect of ionic and osmotic strength on the thermal stability of a trivalent vaccine, M-M-R®II. The control stabilizer is a known stabilizer, disclosed in U.S. Pat. No. 4,273,762, issued to McAleer, et al. This control stabilizer contains the components disclosed in U.S. Pat. No. 4,147,772, issued to McAleer, et al, as well as minute amounts of DPG solution (50 mg ascorbic acid, 100 mg L-cysteine, 50 mg glutathione followed by the addition of 900 ml double distilled $H_2O$, 10 ml of 95% ethyl alcohol, 5 ml polysorbate 80 NF, 25 mg vitamin A [crystalline alcohol], followed by 85 ml of double distilled $H_2O$ and 10 g of adenosine triphosphate). The control stabilizer (and stabilizers of differing osmolarity) are added at a 3:1 stabilizer:MMR vaccine ratio. Formulation A is the control stabilizer minus Medium O components; Formulation B is the control stabilizer with 50% Medium O components; Formulation C is the control stabilizer in 75 mM NaCl; Formulation D is the control stabilizer adjusted to 4.5% sucrose; Formulation E is the control stabilizer in 150 mM NaCl.
Figure 4:
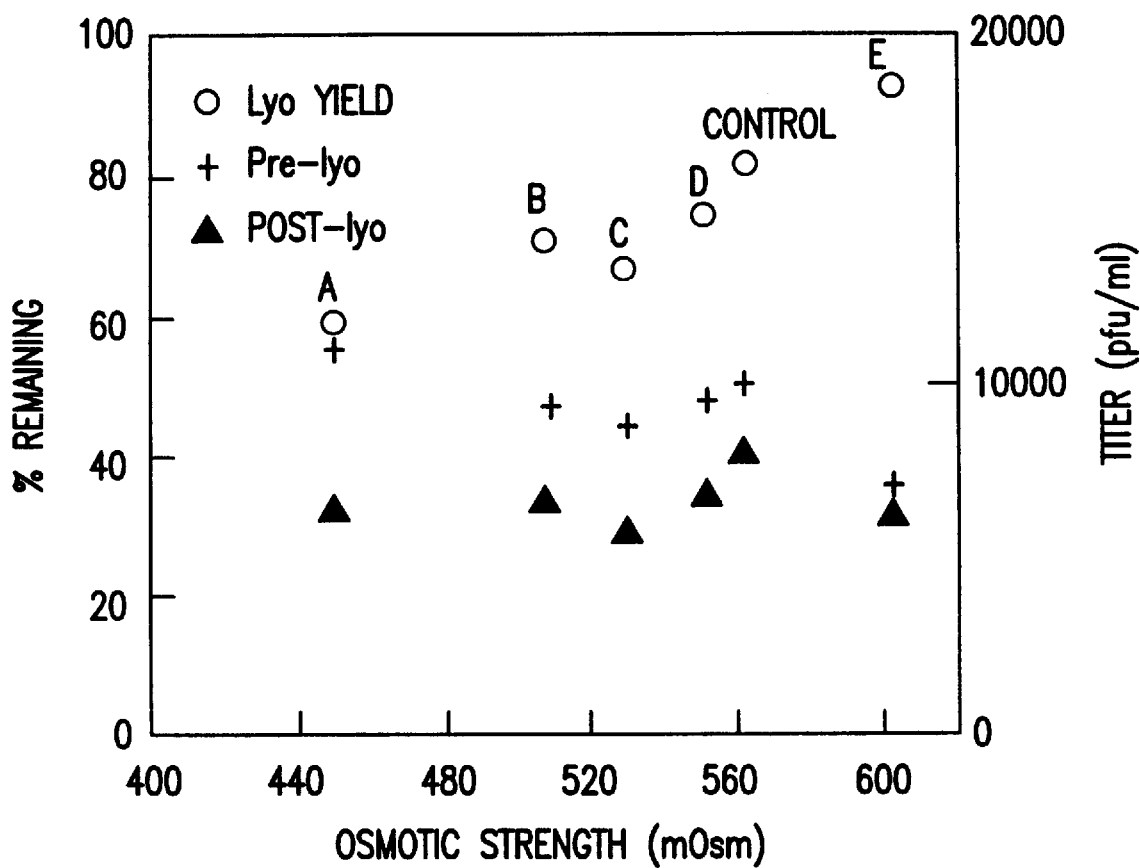
FIG. 4 shows the lyophilization yield of measles virus for the formulations described for FIG. 3.

Effect of Osmotic and Ionic Strength—The effect of ionic and osmotic strength of various formulations (Formulations A–E) on the thermal stability of a measles-mumps-rubella vaccine was evaluated by adjusting the concentration of Medium O or substituting it with either water or saline prior to lyophilizing the vaccine formulation. In addition, similar osmotic strength formulations having different ionic strengths were prepared using half normal saline or 4.5% sucrose in place of Medium O. As shown in FIG. 3, no discernible trend in viral stability at 37° C. was observed for MeV and MuV after one week at 37° C. The stability of RuV appeared more variable, with an indication of increasing stability with increasing osmotic strength. Post-lyophilization titers also were unaffected by changes in osmotic strength in the range of 440–600 mOsm for all viruses. Although the lyophilization yield of MeV appeared to increase with osmotic strength (FIG. 4), there was a concomitant decrease in pre-lyophilization titer resulting in the post-lyophilization titers being equivalent across the osmotic strength range. No trends were evident in the MuV or RuV lyophilization yields. The >100% yields observed in the latter two viruses suggest that the liquid stability of these formulations or handling of the liquid samples resulted in a potency lower than the lyophilized samples (yields ranged from 52–184% for MuV and 102–218% for RuV). The residual moisture contents of these formulations ranged from 1.0–1.4%.

Figure 5:
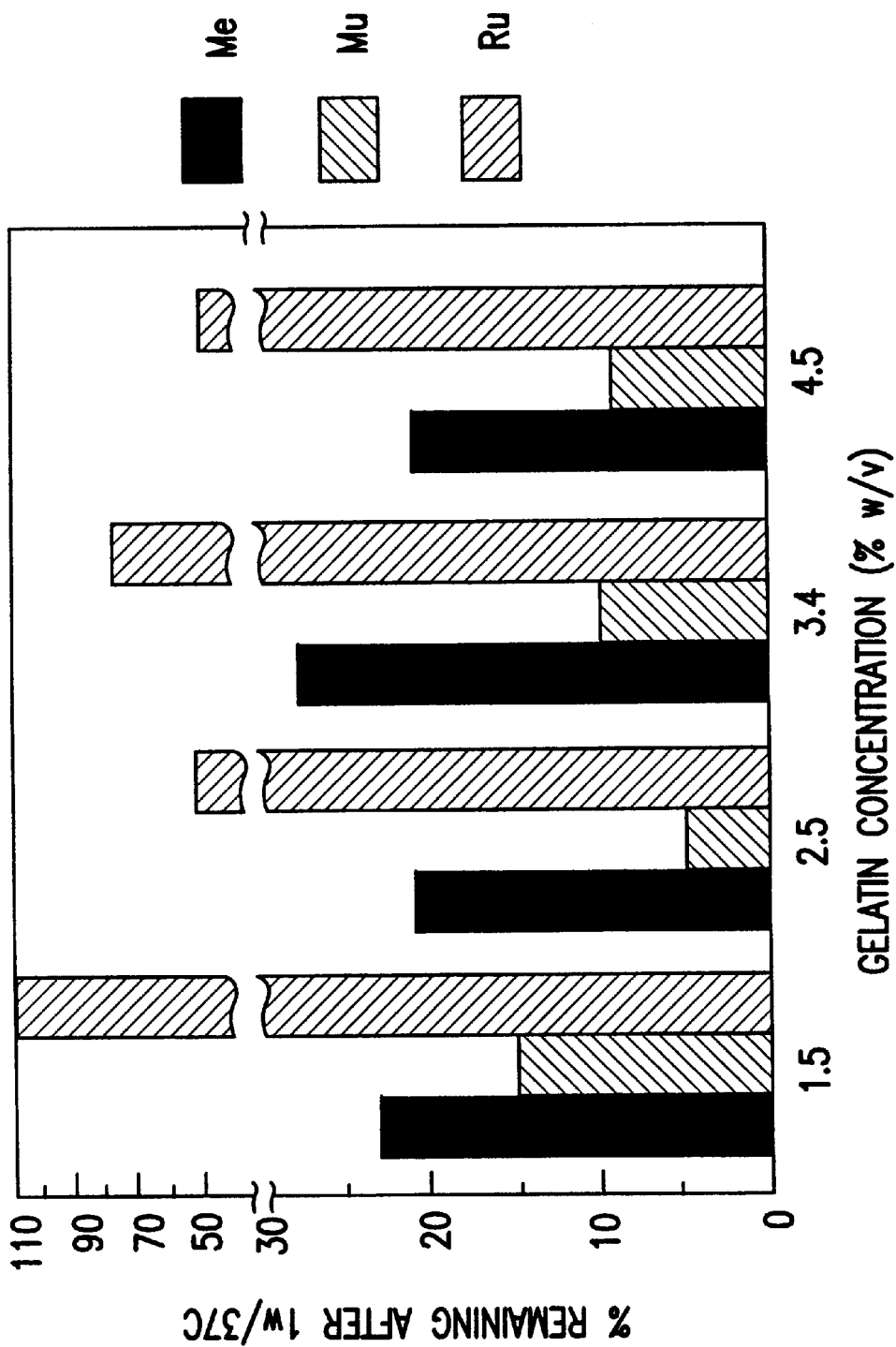
FIG. 5 shows the effect of the hydrolyzed gelatin concentration (1.5–4.5% w/w) on stability of measles, mumps and rubella viruses.

Effect of Hydrolyzed Gelatin Concentration -The effect of the hydrolyzed gelatin concentration (1.5–4.5% w/w) on viral stability was examined. As shown in FIG. 5, changes in the hydrolyzed gelatin concentration (from a control level of 2.5%) show no adverse effect on the thermal stability at 37° C. for all viruses. The lyophilized vaccine containing 1.5% hydrolyzed gelatin showed some shrinkage after incubation for one week at 37° C. All samples contained from 1.0–1.5% moisture indicating that changing the hydrolyzed gelatin concentration does not hamper the drying behavior of the control formulation. Consequently, changes in the hydrolyzed gelatin concentration may be employed to improve the integrity of the lyophilized cake. The lyophilization yields of MeV ranged from 63–104% with formulations containing higher hydrolyzed gelatin contents displaying lower yields. No discernible trends were observed for MuV and RuV which showed lyophilization yields of 54–93%, respectively.

Figure 6A:
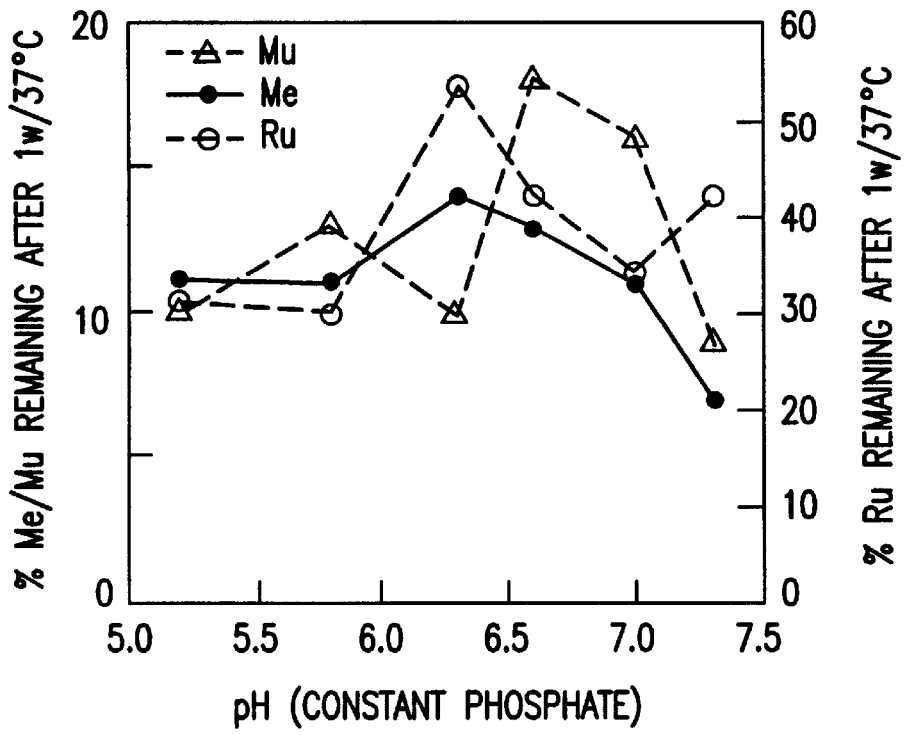
FIGS. 6A and 6B show the effect of buffering capacity on measles, mumps and rubella. Panel A shows the viral stability using a 1M phosphate buffer combine with varying concentration of citrate (0.06–0.40M) to achieve the desired pH. In Panel B both concentrations of phosphate (0.66–0.9M) and citrate (0.03–0.07M) are varied to attain the targeted pH values.
Figure 6B:
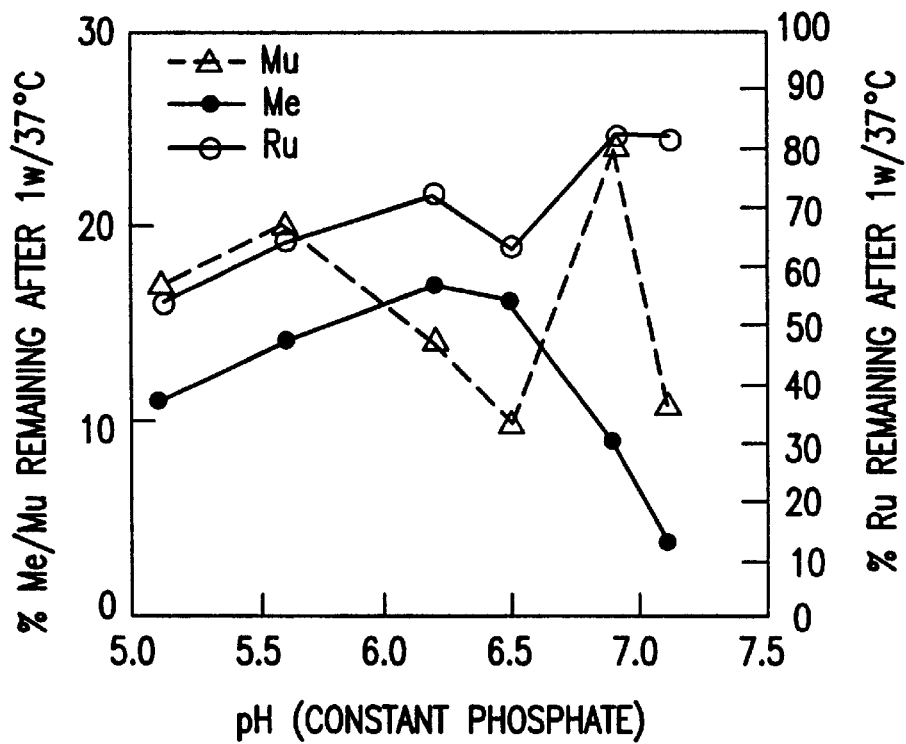

Effect of pH—Citrate-phosphate buffering combinations were tested. Two approaches to the preparation of various pH buffers were examined: a constant phosphate concentration with a variable citrate concentration (resulting in variable ionic strength), and variable concentrations of both buffers (smaller ionic strength changes, but variable phosphate concentration). In formulations prepared using a constant 1.0 M sodium phosphate stock solution and varying concentrations of sodium citrate stock solutions (0.06–0.40 M to achieve the desired pH), MeV appears to have maximum thermal stability at pH 6.3. However, the pH dependence is minimal (FIG. 6A). When concentrations of both citrate and phosphate stock solutions are varied to achieve the desired pH (0.66–0.91 M phosphate and 0.03–0.07 M citrate), a similar pH maximum of 6.2 is observed with MeV thermal stability with the effect decreasing more dramatically at lower and higher pH (FIG. 6B). No clear trend in MuV stability was observed, although these data are the most variable among the three viruses. RuV shows maximum stability at pH 6.2 when 1.0 M phosphate in combination with citrate is used, however, the stability appears to increase at higher pH when variable concentrations of phosphate are employed. An increased phosphate concentration may be surmised to affect viral stability under these circumstances. Residual moisture contents ranged from 1.1–1.6% for all samples. Lyophilization yields showed no dependence on pH for formulations containing 1 M phosphate; however, yields were affected by pH in the pH series where the phosphate was varied. MeV yields appeared to increase as the pH increased although the data is imprecise (lyophilization yields ranged from 58–98%). No clear trends were observed for lyophilization yields in either MuV (58–284%) or RuV (89–131%; greater yields, were observed at lower pH although titers decreased).

Figure 7A:
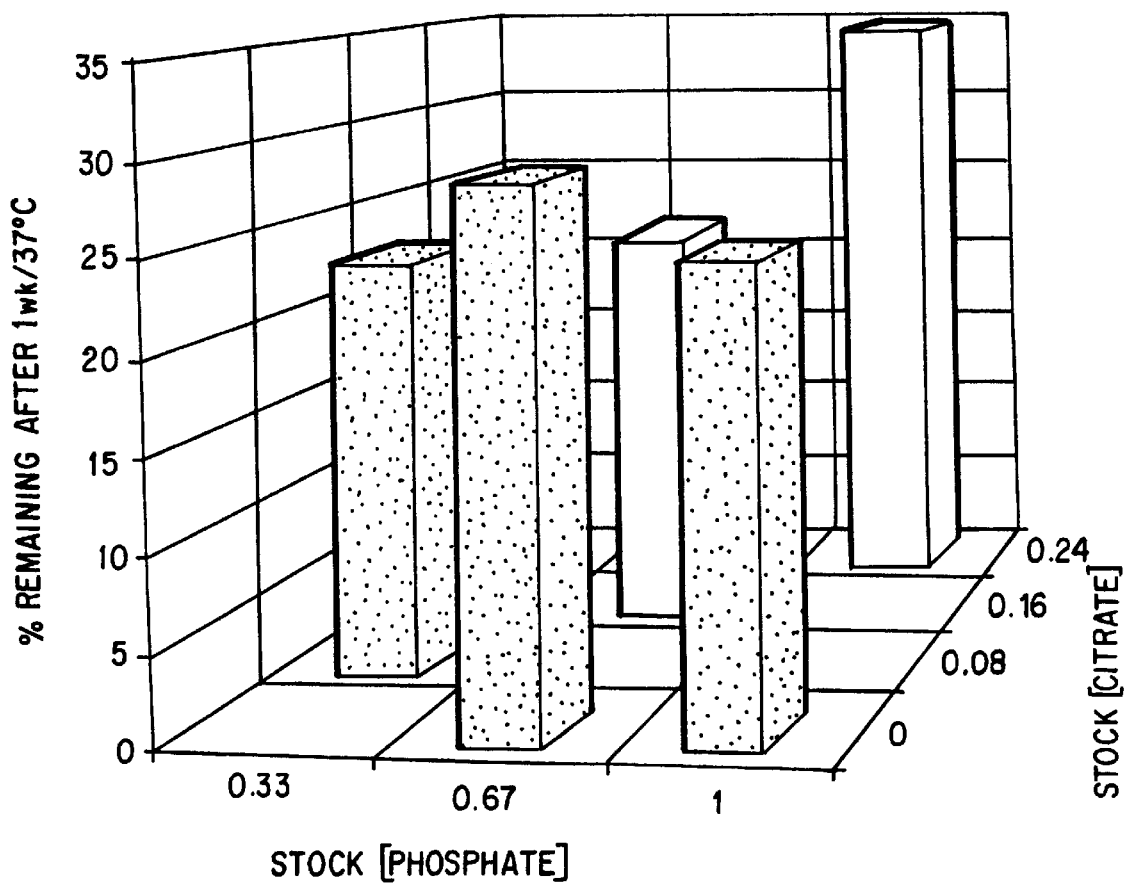
FIGS. 7A–7C show the effect of buffer concentration on viral stability in a stabilizer without bicarbonate. Combinations ranged from between pH 6.2–6.4. All concentrations are those of stock solutions prior to dilution in the final vaccine formulation. Panel A- measles virus; Panel B-mumps virus, Panel C-rubella virus.
Figure 7B:
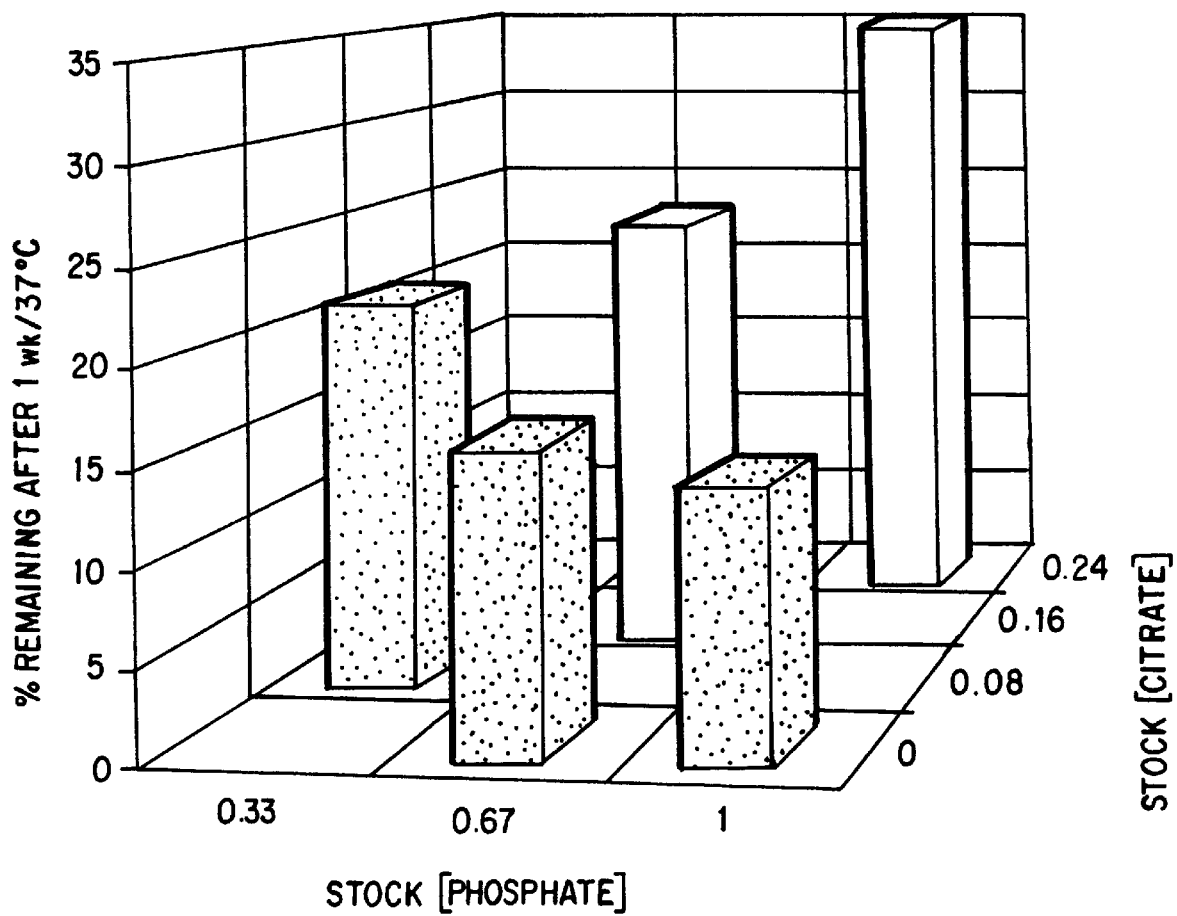
Figure 7C:
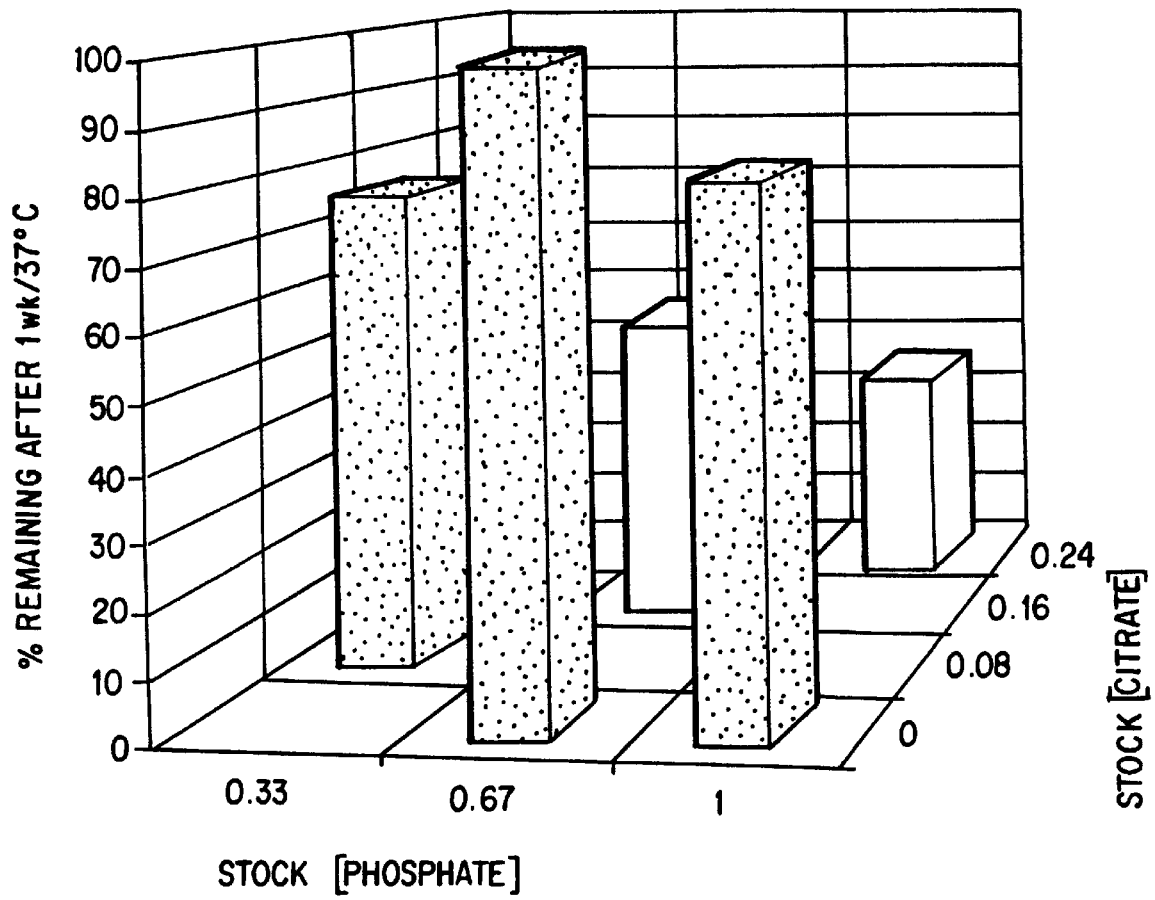

Effect of Buffer Concentration—Sodium bicarbonate was removed from Medium O in various concentrations of phosphate and phosphate/citrate buffers were examined to determine if a lower buffer concentration would be able to control pH or affect virus thermal stability. When maintaining the pH between pH 6.2–6.4, the thermal stability of MeV is not significantly different between the various buffer concentrations (FIG. 7A). However, MuV appears to show increased thermal stability as the citrate concentration is increased (FIG. 7B). The thermal stability of RuV shows no clear trend with phosphate or citrate concentration (FIG. 7C). Moisture contents of the lyophilized products ranged from 0.9–1.9%. No relationship between lyophilization yield and buffer concentration was observed with yields ranging between 50–158% for all viruses.

Figure 8:
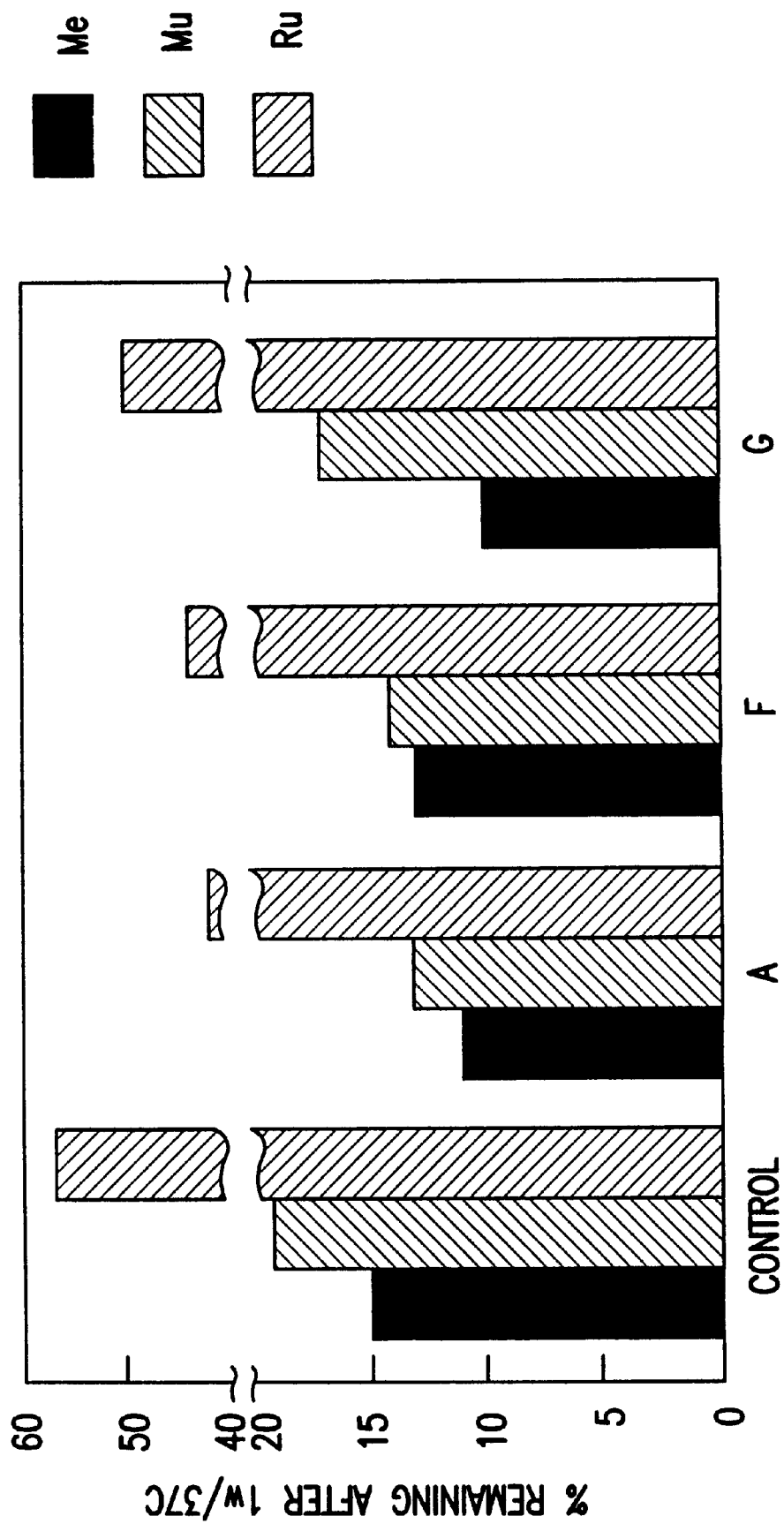
FIG. 8 shows the effect of replacing cell culture medium from the viral stabilizer. The control stabilizer is the stabilizer as described for FIG. 3. Formulation A is the stabilizer as described for FIG. 3. Formulation F is the control stabilizer wherein Medium O was substituted with either Solution 199; Formulation G is the control stabilizer with a mixture of amino acids similar (but not identical) to that found in Medium O of the control stabilizer.
Figure 11:
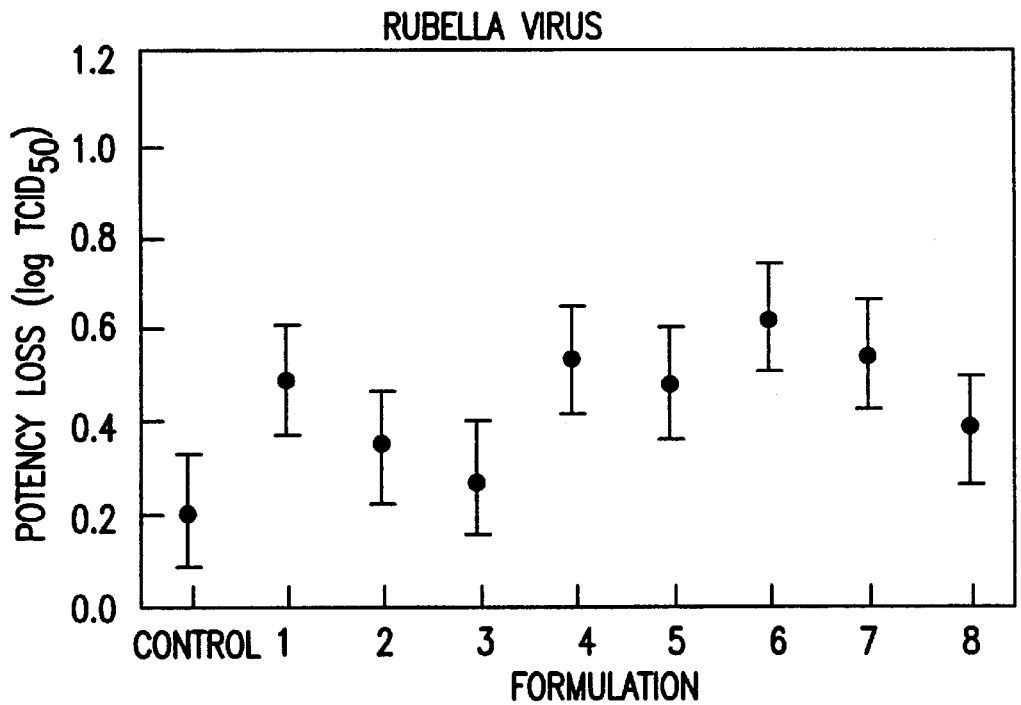
FIG. 11 shows the thermostability of rubella virus for the control stabilizer and Formulation 1- Formulation 8 of Table 1 after post-lyophilization storage for 1 week at 37° C. Increased thermostability is shown as a decrease in potency loss, measured as the log $TCID_{50}$. Bars represent the standard error of the mean.
Figure 12:
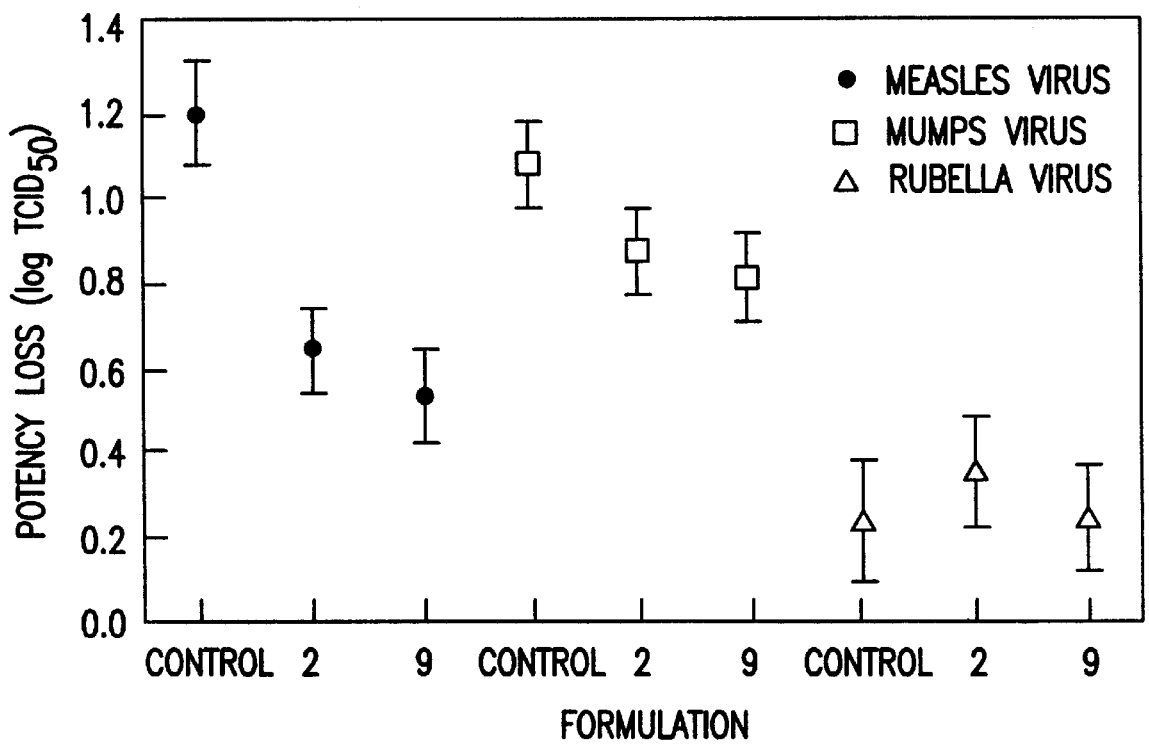
FIG. 12 shows the thermostability of measles, mumps and rubella virus for the control stabilizer (pH 6.6), Formulation 2 (pH 6.8) and Formulation 9 (pH 6.2) of Table 1 after post-lyophilization storage for 1 week at 37° C. Increased thermostability is shown as a decrease in potency loss, measured as the log $TCID_{50}$. Bars represent the standard error of the mean.

Effect of Cell Culture Medium Replacement—The stability of M-M-R®II was examined in various formulations in which subsets of Medium O components were removed or in which Medium O was removed altogether. Medium O was substituted with either water (Formulation A), Medium 199 (Formulation F), or a mixture of amino acids similar (but not identical) to that found in Medium O (Formulation G). Even when the Medium O is removed from the control stabilizer, the final M-M-R®II vaccine still contains Medium O components which are found in the viral bulks. After lyophilization and incubation for one week at 37° C. these variations from the control stabilizer result in slightly lower thermal stability for all viruses (FIG. 8). Removal of Medium O may lower the overall ionic and osmotic strength of the formulation with minimal impact on stability. Also, lower salt concentrations may be necessary to maintain the integrity of the lyophilized product as well as decrease the potential of stinging of these formulations upon injection. No trends were observed in the lyophilization yields of the three viruses (values ranged from 51–141% yields).

Effect of Stoppers on Residual Moisture Content and Stability—Various stopper types and treatments were evaluated to assess the effect of (1) different stoppers on the moisture content of the lyophilized product before and after incubation at 37° C., (2) moisture content on the appearance of the lyophilized product, and (3) moisture content on viral potency. Dried stoppers were prepared by placement in a vacuum oven at 140° C. for 6 hours prior to use. The moisture content of lyophilized vaccine with dried stoppers did not increase after incubation at 37° C. However, stoppers that were not dried resulted in higher moisture content of the lyophilized vaccine after incubation. A higher sugar formulation of the present invention was also examined due to its more hygroscopic nature. The formulation consisted of control stabilizer supplemented with sugars to yield final concentrations of 4.9% sorbitol and 4.4% sucrose. In this case, significant shrinkage was observed in all lyophilized cakes that were incubated at 37° C. with non-dried stoppers. Although the moisture content and physical stability of the lyophilized product is affected by stopper treatment, no clear trend in the viral thermal stability was evident. Consequently, viral stability may not be affected in this range of moisture content with higher sugar concentrations disclosed in the present invention. However, the shrinkage may adversely affect reconstitution of the product and may cause low potency in an assay due to incomplete dissolution and sampling. In a similar manner, lower dosing may result in a clinical setting if there is difficulty in reconstituting the vaccine.

Based on these results obtained from these laboratory-scale experiments, eleven formulations disclosed in Table 1 are exemplified in Example 2 (Formulations 1–9), Example 3 (Formulations 10–11) and Example 4 (Formulation 12). The substantial increase of both sorbitol and sucrose concentrations in the vaccine formulations of the present invention demonstrate dramatic improvement in thermal stability of the measles virus. Cell culture media was eliminated from several vaccine formulations of the present invention to decrease the content of total solids in the formulations. The removal of cell culture media from the stabilizer improves the drying characteristics of high sugar formulations by reducing the total solids content. Furthermore, salts, especially sodium chloride, can substantially lower the glass transition temperature of sugars and increase the potential for the formulation to collapse during lyophilization. Also, lowering the osmolality of the formulations may reduce potential stinging upon injection. Finally, the correlation between pH and thermal stability of MeV is documented in this disclosure. The pH of the preferred formulations 1–12 is adjusted to 6.2 for MeV and pH range of 6.2–6.8 for a combined measles-mumps-rubella vaccine using either a modified sodium phosphate buffer or a sodium phosphate/sodium citrate buffer to minimize the chance of high pH excursions.

EXAMPLE 2

Table 1 shows the concentration of the major components which comprise final vaccine formulations 1–12 of the present invention. Each final vaccine formulation was tested for thermostability. Formulations 1–11 were tested as described throughout Example 1 and Example 3 and Formulation 12 was tested as described in Example 4.

TABLE 1

Components of Formulations 1–12 (grams/liter)

| | hGelatin | Sorbitol | Phosphate | NaCl | Sucrose | Bicarb | Glucose | HSA | Citrate |
|---|---|---|---|---|---|---|---|---|---|
| 1 | 28.94 | 48.94 | 10.59 | 4.92 | 43.74 | 0.34 | 0.66 | 0.62 | 2.53 |
| 2 | 28.94 | 48.94 | 10.59 | 4.92 | 43.74 | 0.34 | 0.66 | 0.62 | 0 |
| 3 | 28.94 | 48.94 | 10.59 | 1.54 | 43.74 | 0.34 | 0.20 | 0.62 | 2.53 |
| 4 | 28.94 | 48.94 | 10.59 | 1.54 | 43.74 | 0.34 | 0.20 | 0.62 | 0 |
| 5 | 28.94 | 48.94 | 10.59 | 4.92 | 23.74 | 0.34 | 0.66 | 0.62 | 2.53 |
| 6 | 28.94 | 48.94 | 10.59 | 1.54 | 23.74 | 0.34 | 0.20 | 0.62 | 2.53 |
| 7 | 28.94 | 58.94 | 10.59 | 1.54 | 33.74 | 0.34 | 0.20 | 0.62 | 0 |
| 8 | 28.94 | 58.94 | 10.59 | 4.92 | 33.74 | 0.34 | 0.66 | 0.62 | 0 |
| 9 | 28.94 | 48.94 | 10.59 | 4.92 | 43.74 | 0.92 | 0.66 | 0.62 | 0 |
| 10 | 28.94 | 48.94 | 10.59 | 1.54 | 3.74 | 0.34 | 0.20 | 0.62 | 2.53 |
| 11 | 28.94 | 48.94 | 10.59 | 4.92 | 43.74 | 0.92 | 0.66 | 0.62 | 2.53 |
| 12 | 28.94 | 58.94 | 10.59 | 4.92 | 43.74 | 0.92 | 0.66 | 0.62 | 2.53 |

TABLE 2

Stabilizers (S1–S12) Corresponding to MMR Vaccine Formulations 1–12 (grams/liter) at 3:1 Stabilizer/Buffer: Virus Ratio

| | hGelatin | Sorbitol | NaCl | Sucrose | Bicarb | Glucose | Citrate |
|---|---|---|---|---|---|---|---|
| S1 | 26.8 | 46.8 | 3.38 | 40.00 | 0 | 0.46 | 2.53 |
| S2 | 26.8 | 46.8 | 3.38 | 40.00 | 0 | 0.46 | 0 |
| S3 | 26.8 | 46.8 | 0 | 40.00 | 0 | 0 | 2.53 |
| S4 | 26.8 | 46.8 | 0 | 40.00 | 0 | 0 | 0 |
| S5 | 26.8 | 46.8 | 3.38 | 20.00 | 0 | 0.46 | 2.53 |
| S6 | 26.8 | 46.8 | 0 | 20.00 | 0 | 0 | 2.53 |
| S7 | 26.8 | 56.8 | 0 | 30.00 | 0 | 0 | 0 |
| S8 | 26.8 | 56.8 | 3.38 | 30.00 | 0 | 0.46 | 0 |
| S9 | 26.8 | 46.8 | 3.38 | 40.00 | 0.59 | 0.46 | 0 |
| S10 | 26.8 | 46.8 | 0 | 0 | 0 | 0 | 2.53 |
| S11 | 26.8 | 46.8 | 3.38 | 40.00 | 0.59 | 0.46 | 2.53 |
| S12 | 26.8 | 56.8 | 3.38 | 30.00 | 0.59 | 0.46 | 0 |

A preferred vaccine of the present invention is a measles-munpss-rubella trivalent vaccine. Such a preferred measles-mumps-rubella trivalent vaccine of the present invention will comprise at least the major components of Formulations 1–12 of Table 1. Alternatively, major components such a hydrolyzed gelatin, sucrose, sorbitol, phosphate or a phosphate:citrate combination may be added to a vaccine formulation in the respective ranges disclosed throughout this specification. These erred measles-mumps-rubella will commonly be mixed in a 3:1 stabilizer/buffer:virus combination. In these exemplified trivalent formulations, approximately 2.1 g/l of hydrolyzed gelatin, 2.1 g/l of sorbitol, 3.7 g/l of sucrose, and 1.54 g/l of NaCl are present in the viral media. Aditionally, the stabilizer may be added at 67.5% of the final volume of the vaccine formulation with the addition of a phosphate buffer or phosphate:citrate combination comprising 7.5% of the final volume of the vaccine formulation. Therefore, components of preferred stabilizer solutions for use in such a stabilizer/buffer virus combination are easily determined on the basis of the initial contribution of components from both the viral containing media and buffer. Table 2 shows the major components of a vaccine associated with Formulations 1–12 of the present invention.

Neomycin may be added to any of the formulations of the present invention in a biologically active amount, preferably about 0.34 ml of a stock USP solution of neomycin. Phenol red may also be added, preferably at about 0.01 g/l. Solution DPG and/or Solution 199 may be added at a biologically active level, preferably from about 0.1 to about 2.0 ml of each respective stock solution. Human serum albumin may be replaced by any available biological equivalent.

Table 1 shows that the major components of a lyophilized vaccine of the present invention may be present in varying percentage of dry weight of the lyophilized vaccine. Regarding Formulations 1–12, hydrolyzed gelatin is present from about 20% to about 30% total dry weight, sorbitol is present from about 35% to about 50% total dry weight, phosphate is present from about 7.5% to about 10% total dry weight, sodium chloride is present from about 1% to about 4% total dry weight, sodium bicarbonate is present from about 0.2% to about 0.7% total dry weight, sodium citrate is present up to about 3% and human serum albumin is present from about 0.4% to about 0.7% total dry weight.

Final vaccine formulations 1–8 show increased thermostability for measles virus (FIG. 9) in comparison to the control stabilizer, comparable thermostability of mumps virus (FIG. 10) and slightly decreased thermostability for rubella virus (FIG. 11) subsequent to lyophliztion.

The thermostability of formulation 9 was compared to formulation 2. This experiment compared the effect of additionally added sodium bicarbonate to the thermostability of the lyophilized formulation. FIG. 12 shows a marked increase in thermostability of measles virus in either formulation 9 or formulation 2 (see also FIG. 9). FIG. 12 also shows that thermostability of mumps virus in formulation 9 and formulation 2 is comparable (also, see FIG. 10 regarding formulation 2). Finally, FIG. 12 also shows that thermostability of rubella virus for the control stabilizer, formulation 9 and formulation 2 are comparable (see FIG. 11 regarding formulation 2).

Formulations 1–9 exemplify various ranges of respective compounds disclosed in the present invention. Formulations 1–9 show increases in thermostability of the measles virus while not adversely effecting thermostability of either the mumps virus or the rubella virus.

EXAMPLE 3

A fill and lyophilization of Formulation 10, Formulation 11 and the control stabilizer were performed essentially as described herein. Both Formulation 10 and Formulation 11 improved the thermostability of measles virus from a 0.9 log loss (after 1 week at 37° C.) to 0.6 log loss when compared with the control stabilizer. The thermal stability of mumps and rubella virus components were within 0.1 log loss of the control stabilizer. The thermal stability showed no dependence on the location on the shelf or within individual trays. Adjustment of the placement of thermocouples in the lyophilization cabinet resulted in more uniform temperature readings and monitoring of many lyophilization parameters which allowed an unambiguous determination of the end of primary drying during the lyophilization cycle. Although absolute potencies differed in the $TCID_{50}$ and plaque assays, the relative potencies (hence the log losses) for similar samples were comparable in both assays. Vaccine frozen by different methods (shelf or liquid nitrogen tunnel) showed different drying rates and microscopic morphology.

Methods—Formulations—Three stabilizer formulations were selected for a scale-up run. The first stabilizer was the control stabilizer. The second formulation was Formulation 10 and a third formulation was Formulation 11 (Table 1) Each of these formulations contains 4.9% sorbitol in the final vaccine, however the formulations possess different osmolarities and solids contents. Formulation 11 contains 4.9% sorbitol and 4.4% sucrose in the final vaccine. Formulation 10 consists of control stabilizer absent cell culture medium, with 4.9% sorbitol in the final vaccine. Formulation 10 possesses a lower osmolality which may decrease potential stinging upon injection and may facilitate the lyophilization process due to the lower concentrations of salts. Sodium phosphate buffer (1 M, pH 6.2) was used to buffer the pH of control stabilizer to a value of 6.5. Sodium phosphate/sodium citrate buffer (142 g/L sodium phosphate dibasic, anhydrous +50.0 g/L citric acid, anhydrous) maintains the pH of Formulation 9 and Formulation 10 at 6.2.

The stoppers used to seal the product vials were West 1816 stoppers further dried (140° C. for 6 h) to prevent any desorption of moisture into the dried product. Each of the three stabilizers described above were prepared with stabilizer, buffer, and viral bulks. Eight perforated trays of vials were filled with each of the formulations, frozen in a liquid nitrogen tunnel, and loaded onto one of the middle three shelves of the pre-chilled lyophilization cabinet. The lyophilization parameters minimized any potential physical effects that the current aggressive production cycle may have on the high sugar formulations. After the freezing process, the shelf temperature was increased to −15° C. to rapidly raise the product temperature before the shelf was decreased to −25° C. for the remainder of primary drying. In this manner, the product temperature was kept near −40° C. during all of primary drying to minimize the potential risk of product collapse. When the primary drying finished, the shelf temperature was elevated to 30° C. at a rate of 3° C./h and then maintained there for 10 h. The shelf temperature may be elevated from a rate of about 3° C./h to about 6° C./h. The duration at such temperature was required to reach a very low moisture content in the high sugar product, which is essential to maintain the physical integrity of the cake during 37° C. incubation. There was a total of twelve thermocouples available in the lyophilization cabinet to monitor the lyophilization process. In addition, the thermocouple vials were placed away from the ring of the tray (approximately 12 rows from the front and at least 6 rows from the sides). Pre-lyophilization liquid) samples were collected during the beginning, middle and end of the filling process to examine any degradation of viral potency. They were frozen in the liquid nitrogen tunnel per the normal production process. Two types of samples were retrieved from the trays after lyophilization. The first set of samples denoted as "edge" samples were vials selected within 2 rows adjacent to the edge of the ring. Another set of samples denoted as "random" samples were vials randomly collected from more than 2 rows away from the edge of the ring. Samples were also collected from different trays on the same lyophilizer shelf. Trays 1–4 occupy the backside of a shelf left to right, and trays 5–8 are located in the front half of the shelf.

Potencies for all three viruses were determined using a TCID$_{50}$ assay or a plaque assay. These assays were all performed in a 1×6 format, i.e., one vial in 6 unique setups, such as different times or days. Moisture content of lyophilized product was measured using the Karl Fisher method and represent the average of 4 vials.

Moisture Content and pH—The moisture content of each formulation was fairly uniform across trays. The moisture contents attained in this large-scale run are similar to the range of values obtained from samples generated at the laboratory scale. Moisture contents ranged from 0.4–0.8% for all formulations. No significant moisture uptake or cake collapse were observed in the formulations before or after a one-week incubation at 37° C. (Table 3). Thus, the drying method of stoppers is sufficient prevent moisture transfer to the lyophilized product. The pH of the final vaccine was 6.5 for the control stabilizer, 6.2 for Formulation 10 and 6.3 for Formulation 11.

TABLE 3

Moisture content (%) of lyophilized products before and after 1-week incubation at 37° C.

|  | −70° C. storage | After incubation at 37° C. for 1 week |
|---|---|---|
| Control | 0.4 | 0.5 |
| Form. 10 | 0.3 | 0.4 |
| Form. 11 | 0.6 | 0.6 |

Thermostability and Lyophilization Yields—Averaging 90 determinations of thermostability (90 vials unincubated +90 vials incubated at 37° C. for one week). As seen in Example 1 and Example 2 for Formulations 1–9, Formulations 10 and 11 show improved stability of measles virus relative to M-M-R®II in the control stabilizer (Table 4). For Formulations 10 and 11, no vials lost more than 0.9 logs of measles potency after the incubation period. The thermostabilities of mumps and rubella viruses appear to be relatively unaffected by the formulation changes. Absolute potency values and lyophilization yields were comparable for the three formulations tested (Table 5).

TABLE 4

Log loss (and range of observed values) in viral potency after one week at 37° C.

|  | MeV | | MuV | | RuV | |
|---|---|---|---|---|---|---|
| Cont | 0.9 | (0.7–1.1) | 1.0 | (0.7–1.1) | 0.1 | (0.0–0.4) |
| F. 10 | 0.6 | (0.5–0.9) | 0.9 | (0.7–1.0) | 0.2 | (0.0–0.6) |
| F. 11 | 0.6 | (0.4–0.8) | 0.9 | (0.6–1.1) | 0.1 | (0.0–0.6) |

TABLE 5

Mean titers (TCID$_{50}$/mL) of lyophilized vaccine and losses observed across lyophilization and filling.

|  | MeV Titer | Log loss | MuV Titer | Log loss | RuV Titer | Log loss |
|---|---|---|---|---|---|---|
| Cont | 4.1 | 0.2 | 5.1 | 0.3 | 4.0 | 0.1 |
| F. 10 | 4.0 | 0.2 | 5.1 | 0.3 | 3.6 | 0.1 |
| F. 11 | 4.1 | 0.3 | 5.1 | 0.4 | 4.0 | −0.2 |

Potencies of the liquid samples collected during the beginning, middle, and end of the fill are similar and suggest that no significant degradation is taking place over the course of the fill (ca. 1 h at 4° C.). The mean loss in potencies were uniform with respect to tray location on the lyophilizer shelf and vial location within trays.

Table 6 shows the log loss in titer for the control formulation, Formulation 10 and Formulation 11.

TABLE 6

Comparison of viral potency losses observed in the TCID$_{50}$ and plaque (PFU) assays. The values represent the log loss in viral titer after incubation for one week at 37° C. averaged over three different trays as well as both vial locations within a tray.

|  | Control | | Form. 10 | | Form. 11 | |
|---|---|---|---|---|---|---|
|  | TCID$_{50}$ | PFU | TCID$_{50}$ | PFU | TCID$_{50}$ | PFU |
| MeV | 0.95 | 0.83 | 0.77 | 0.62 | 0.65 | 0.53 |
| MuV | 1.02 | 1.05 | 0.88 | 0.95 | 0.82 | 0.92 |
| RuV | 0.18 | 0.08 | 0.33 | 0.42 | 0.37 | 0.05 |

Measles virus in the control stabilizer shows better stability when frozen in liquid nitrogen when compared to vaccine which was frozen on the shelf. However, MeV stability in Formulation 10 and Formulation 11 are comparable with either freezing methods. Stability of MuV and RuV do not differ to a significant extent when either of the freezing methods are used (Table 7). Standard deviations of the values obtained for potency losses were 0.1 for MeV, 0.2 for MuV, and 0.1 for RuV.

TABLE 7

Potency Loss (and range of observed values) after 1 week at 37° C.

| Formulation | MeV | | MuV | | RuV | |
|---|---|---|---|---|---|---|
| Shelf frozen | | | | | | |
| Control | 1.0 | (0.9–1.0) | 0.9 | (0.7–1.2) | 0.0 | (−0.5–0.2) |
| Form. 10 | 0.5 | (0.4–0.5) | 0.7 | (0.5–0.8) | 0.7 | (0.5–0.9) |
| Form. 11 | 0.5 | (0.3–0.6) | 0.7 | (0.6–0.9) | 0.2 | (0.1–0.4) |
| Liquid N$_2$ frozen | | | | | | |
| Control | 0.7 | (0.6–0.8) | 0.8 | (0.5–1.1) | 0.0 | (0.0–0.1) |
| Form. 10 | 0.4 | (0.3–0.5) | 0.7 | (0.6–0.9) | 0.5 | (0.3–0.7) |
| Form. 11 | 0.4 | (0.3–0.6) | 0.8 | (0.6–1.1) | 0.1 | (−0.1–0.2) |

EXAMPLE 4

Figure 13:
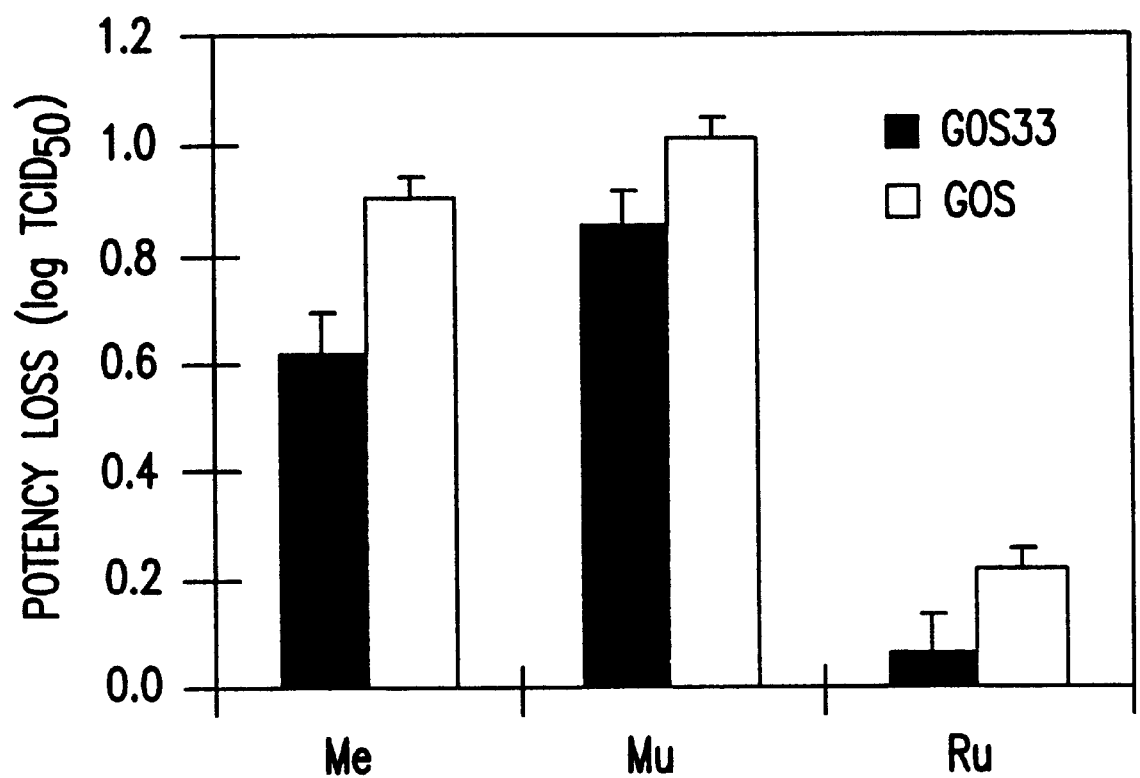
FIG. 13 shows enhancement of viral stability with a GOS33 formulation as described as formulation #12 of Table 1 and S12 of Table 2 compared with GOS (control stabilizer). Experimental runs utilized a 0.5 ml fill for GOS33 compared to separate runs using a 0.7 ml fill for GOS. Increased thermostability is shown as a decrease in potency loss, measured as the log $TCID_{50}$. Bars represent the standard error of the mean.
Figure 14:
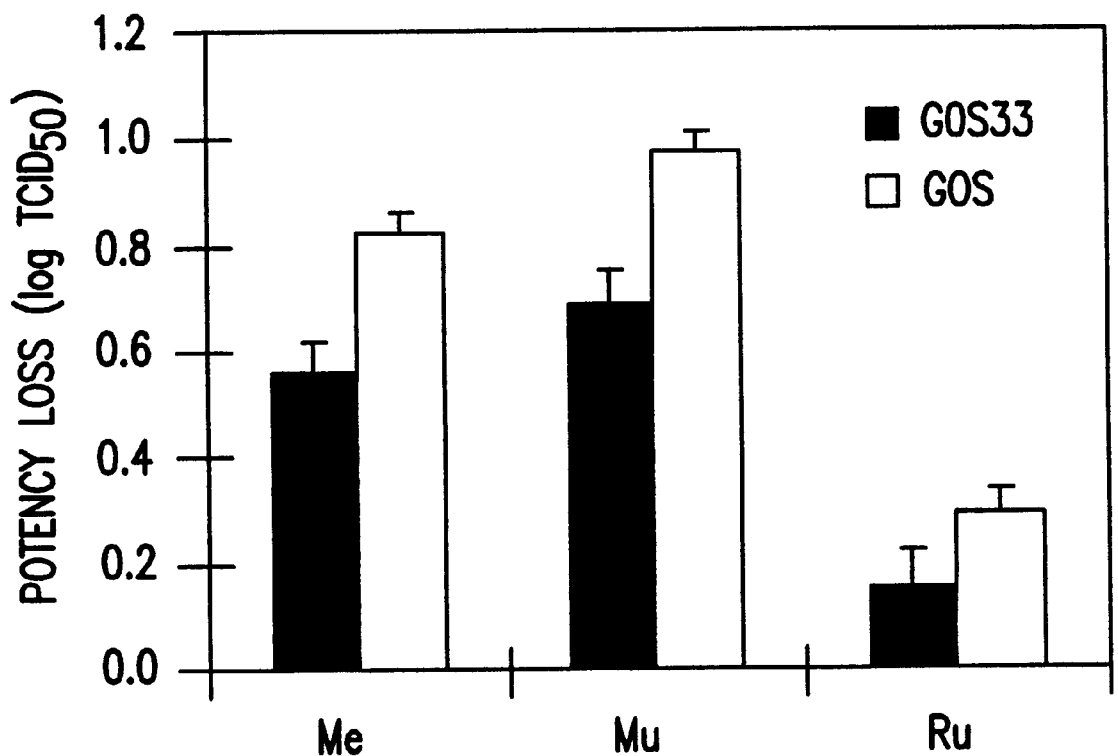
FIG. 14 shows enhancement of viral stability with a GOS33 formulation as described as formulation #12 of Table 1 and S12 of Table 2 compared with GOS (control stabilizer). Experimental runs utilized a 0.7 ml fill volume. Increased thermostability is shown as a decrease in potency loss, measured as the log $TCID_{50}$. Bars represent the standard error of the mean.

An especially preferred formulation of the present invention is depicted as Formulation 12 in Table 1 and S12 in Table 2. The materials and methods from Examples 1–3 may be utilized in generating the data of this example. The lyophilization cycle is as follows: after the vaccine is formulated with stabilizer, buffer and viral bulks, 0.5 ml is placed in a 3 ml glass vial with stoppers loosely placed in the vial to allow for escape of water vapor during lyophilization. The vials are loaded onto a perforated tray and passed through a liquid nitrogen tunnel to affect freezing. The trays are then loaded onto a lyophilizer shelf that has been cooled to ca. −50° C. After loading the lyophilization cabinet and starting the lyophilization cycle, the shelf temperature is increased to −25° C. and maintained for the remainder of primary drying. In this manner, the product temperature was kept near −40° C. during all of primary drying to minimize the potential risk of product collapse. At the end of primary drying, thermocouples placed in the vaccine vials are observed to undergo a rapid increase in temperature after bulk ice has sublimed. The shelf temperature was then elevated to 32° C. at a rate of 6° C./h and maintained there for 15 hours. The duration at such a temperature promotes reaching a very low moisture content in the high sugar product, which maintains the physical integrity of the cake during 37° C. incubation. The skilled artisan will be aware that this lyophilization procedure may be interchanged with the procedure disclosed in Example 1–3, while the formulation of this Example may also be used in conjunction with a lyophilization procedure of Example 1–3. Data showing the enhancement of viral stability using this formulation is shown in FIG. 13 (0.5 ml fill) and FIG. 14 (0.7 ml fill).

What is claimed is:

1. A vaccine comprising an attenuated virus and stabilizer, wherein said vaccine comprises
   28.94 grams per liter of hydrolyzed gelatin, 48.94 grams per liter of sorbitol, 10.59 grams per liter of phosphate, 4.92 grams per liter NaCl, 43.74 grams per liter of sucrose, 0.34 grams per liter bicarbonate, 0.66 grams per liter glucose, 0.62 grams per liter HSA, and 2.53 grams per liter of citrate;
   wherein the virus includes at least an attenuated mumps virus.

2. A vaccine comprising an attenuated virus and stabilizer, wherein said vaccine comprises
   28.94 grams per liter of hydrolyzed gelatin, 48.94 grams per liter of sorbitol, 10.59 grams per liter of phosphate, 1.54 grams per liter NaCl, 43.74 grams per liter of sucrose, 0.34 grams per liter bicarbonate, 0.20 grams per liter glucose, 0.62 grams per liter HSA, and 2.53 grams per liter of citrate;
   wherein the virus includes at least an attenuated mumps virus.

3. A vaccine comprising an attenuated virus and stabilizer, wherein said vaccine comprises
   28.94 grams per liter of hydrolyzed gelatin, 48.94 grams per liter of sorbitol, 10.59 grams per liter of phosphate, 1.54 grams per liter NaCl, 43.74 grams per liter of sucrose, 0.34 grams per liter bicarbonate, 0.20 grams per liter glucose, 0.62 grams per liter HSA, and no citrate;
   wherein the virus includes at least an attenuated mumps virus.

4. A vaccine comprising an attenuated virus and stabilizer, wherein said vaccine comprises
   28.94 grams per liter of hydrolyzed gelatin, 48.94 grams per liter of sorbitol, 10.59 grams per liter of phosphate, 4.92 grams per liter NaCl, 43.74 grams per liter of sucrose, 0.34 grams per liter bicarbonate, 0.66 grams per liter glucose, 0.62 grams per liter HSA, and no citrate;
   wherein the virus includes at least an attenuated mumps virus.

5. A lyophilized vaccine of claim 2.
6. A lyophilized vaccine of claim 3.
7. A lyophilized vaccine of claim 4.
8. A lyophilized vaccine of claim 1.
9. A stabilized vaccine obtained by reconstituting said lyophilized vaccine of claim 5.
10. A stabilized vaccine obtained by reconstituting said lyophilized vaccine of claim 6.
11. A stabilized vaccine obtained by reconstituting said lyophilized vaccine of claim 7.
12. A stabilized vaccine obtained by reconstituting said lyophilized vaccine of claim 8.
13. A vaccine comprising at least an attenuated mumps virus and vaccine stabilizer selected from the group consisting of
    (a) a vaccine comprising 26.8 grams per liter of hydrolyzed gelatin, 46.8 grams per liter of sorbitol, 3.38 grams per liter NaCl, 40 grams per liter of sucrose, no bicarbonate, 0.46 grams per liter glucose, and 2.53 grams per liter citrate;
    (b) a vaccine comprising 26.8 grams per liter of hydrolyzed gelatin, 46.8 grams per liter of sorbitol, 3.38 grams per liter NaCl, 40 grams per liter of sucrose, no bicarbonate, 0.46 grams per liter glucose, and no citrate;
    (c) a vaccine comprising 26.8 grams per liter of hydrolyzed gelatin, 46.8 grams per liter of sorbitol, no NaCl, 40 grams per liter of sucrose, no bicarbonate, no glucose, and 2.53 grams per liter citrate;
    (d) a vaccine comprising 26.8 grams per liter of hydrolyzed gelatin, 46.8 grams per liter of sorbitol, no NaCl, 40 grams per liter of sucrose, no bicarbonate, no glucose, and no citrate;
    (e) a vaccine comprising 26.8 grams per liter of hydrolyzed gelatin, 46.8 grams per liter of sorbitol, 3.38 grams per liter NaCl, 40 grams per liter of sucrose, 0.59 grams per liter bicarbonate, 0.46 grams per liter glucose, and no citrate; and
    (f) a vaccine comprising 26.8 grams per liter of hydrolyzed gelatin, 46.8 grams per liter of sorbitol, 3.38 grams per liter NaCl, 40 grams per liter sucrose, 0.59 grams per liter bicarbonate, 0.46 grams per liter glucose, and 2.53 grams per liter citrate.

14. A method of preparing a lyophilized form of a vaccine which is effectively reconstituted for host inoculation, which comprises:
    a) drying a vial stopper;
    b) sealing a vial containing the vaccine formulation with the vial stopper;
    c) lyophilizing the sealed vial containing the vaccine formulation, resulting in the lyophilized form of the vaccine with a moisture content from about 0.4% to about 0.8%; and,
    d) resuspending the lyophilized form of the vaccine
    wherein the vaccine comprises at least an attenuated mumps virus and stabilizer selected from the group consisting of
    (a) a vaccine comprising 28.94 grams per liter of hydrolyzed gelatin, 48.94 grams per liter of sorbitol, 10.59 grams per liter of phosphate, 4.92 grams per liter NaCl, 43.74 grams per liter of sucrose, 0.34 grams per liter bicarbonate, 0.66 grams per liter glucose, 0.62 grams per liter HSA, and 2.53 grams per liter of citrate;
    (b) a vaccine comprising 28.94 grams per liter of hydrolyzed gelatin, 48.94 grams per liter of sorbitol, 10.59 grams per liter of phosphate, 4.92 grams per liter NaCl, 43.74 grams per liter of sucrose, 0.34 grams per liter bicarbonate, 0.66 grams per liter glucose, 0.62 grams per liter HSA, and no citrate;
    (c) a vaccine comprising 28.94 grams per liter of hydrolyzed gelatin, 48.94 grams per liter of sorbitol, 10.59 grams per liter of phosphate, 1.54 grams per liter NaCl, 43.74 grams per liter of sucrose, 0.34 grams per liter bicarbonate, 0.20 grams per liter glucose, 0.62 grams per liter HSA, and 2.53 grams per liter of citrate;
    (d) a vaccine comprising 28.94 grams per liter of hydrolyzed gelatin, 48.94 grams per liter of sorbitol, 10.59 grams per liter of phosphate, 1.54 grams per liter NaCl, 43.74 grams per liter of sucrose, 0.34 grams per liter bicarbonate, 0.20 grams per liter glucose, 0.62 grams per liter HSA, and no citrate;
    (e) a vaccine comprising 28.94 grams per liter of hydrolyzed gelatin, 48.94 grams per liter of sorbitol, 10.59 grams per liter of phosphate, 4.92 grams per liter NaCl, 43.74 grams per liter of sucrose, 0.92 grams per liter bicarbonate, 0.66 grams per liter glucose, 0.62 grams per liter HSA, and no citrate; and (f) a vaccine comprising 28.94 grams per liter of hydrolyzed gelatin, 48.94 grams per liter of sorbitol, 10.59 grams per liter of phosphate, 4.92 grams per liter NaCl, 43.74 grams per liter of sucrose, 0.92 grams per liter bicarbonate, 0.66 grams per liter glucose, 0.62 grams per liter HSA, and 2.53 grams per liter citrate.

15. A method of preparing a lyophilized form of a vaccine which is effectively reconstituted for host inoculation, which comprises:

a) drying a vial stopper;

b) sealing a vial containing the vaccine formulation with the vial stopper;

c) lyophilizing the sealed vial containing the vaccine formulation, resulting in the lyophilized form of the vaccine with a moisture content from about 0.4% to about 0.8% and, d) resuspending the lyophilized form of the vaccine, wherein the lyophilization step comprises:

a) precooling to about −45° C.;

b) initially drying the vaccine formulation by increasing the temperature to about −15° C. and then decreasing the temperature to about −25° C.;

c) elevating the shelf temperature to 30° C. at a rate of about 3° C.–6° C. per hour;

d) maintaining shelf temperature at 30° C. for at least about 10 hours wherein the vaccine comprises at least an attenuated mumps virus and stabilizer selected from the group consisting of:

(a) a vaccine comprising 28.94 grams per liter of hydrolyzed gelatin, 48.94 grams per liter of sorbitol, 10.59 grams per liter of phosphate, 4.92 grams per liter NaCl, 43.74 grams per liter of sucrose, 0.34 grams per liter bicarbonate, 0.66 grams per liter glucose, 0.62 grams per liter HSA, and 2.53 grams per liter of citrate;

(b) a vaccine comprising 28.94 grams per liter of hydrolyzed gelatin, 48.94 grams per liter of sorbitol, 10.59 grams per liter of phosphate, 4.92 grams per liter NaCl, 43.74 grams per liter of sucrose, 0.34 grams per liter bicarbonate, 0.66 grams per liter glucose, 0.62 grams per liter HSA, and no citrate;

(c) a vaccine comprising 28.94 grams per liter of hydrolyzed gelatin, 48.94 grams per liter of sorbitol, 10.59 grams per liter of phosphate, 1.54 grams per liter NaCl, 43.74 grams per liter of sucrose, 0.34 grams per liter bicarbonate, 0.20 grams per liter glucose, 0.62 grams per liter HSA, and 2.53 grams per liter of citrate;

(d) a vaccine comprising 28.94 grams per liter of hydrolyzed gelatin, 48.94 grams per liter of sorbitol, 10.59 grams per liter of phosphate, 1.54 grams per liter NaCl, 43.74 grams per liter of sucrose, 0.34 grams per liter bicarbonate, 0.20 grams per liter glucose, 0.62 grams per liter HSA, and no citrate;

(e) a vaccine comprising 28.94 grams per liter of hydrolyzed gelatin, 48.94 grams per liter of sorbitol, 10.59 grams per liter of phosphate, 4.92 grams per liter NaCl, 43.74 grams per liter of sucrose, 0.92 grams per liter bicarbonate, 0.66 grams per liter glucose, 0.62 grams per liter HSA, and no citrate; and (f) a vaccine comprising 28.94 grams per liter of hydrolyzed gelatin, 48.94 grams per liter of sorbitol, 10.59 grams per liter of phosphate, 4.92 grams per liter NaCl, 43.74 grams per liter of sucrose, 0.92 grams per liter bicarbonate, 0.66 grams per liter glucose, 0.62 grams per liter HSA, and 2.53 grams per liter citrate.

16. A vaccine comprising about 46.8 to 48.94 grams per liter of sorbitol, about 40 to 45 grams per liter of sucrose, gelatin, and at least an attenuated mumps virus.

17. A lyophilized vaccine of claim 16.

18. A stabilized vaccine obtained by reconstituting said lyophilized vaccine of claim 17.

* * * * *